United States Patent
Carlson et al.

(10) Patent No.: US 9,468,595 B2
(45) Date of Patent: *Oct. 18, 2016

(54) ACRYLAMIDE DERIVATIVES

(71) Applicant: EMPIRE TECHNOLOGY DEVELOPMENT LLC, Wilmington, DE (US)

(72) Inventors: William Brenden Carlson, Seattle, WA (US); Gregory David Phelan, Cortland, NY (US)

(73) Assignee: EMPIRE TECHNOLOGY DEVELOPMENT LLC, Wilmington, DE (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/440,344

(22) PCT Filed: Nov. 2, 2012

(86) PCT No.: PCT/US2012/063211
§ 371 (c)(1),
(2) Date: May 1, 2015

(87) PCT Pub. No.: WO2014/070192
PCT Pub. Date: May 8, 2014

(65) Prior Publication Data
US 2015/0272854 A1    Oct. 1, 2015

(51) Int. Cl.
*A61K 8/81* (2006.01)
*A61Q 5/02* (2006.01)
*C08F 220/58* (2006.01)
*A61Q 1/10* (2006.01)
*C08F 120/58* (2006.01)
*A61Q 5/06* (2006.01)
*C08F 222/38* (2006.01)
(Continued)

(52) U.S. Cl.
CPC ............ *A61K 8/8158* (2013.01); *A61Q 1/10* (2013.01); *A61Q 5/02* (2013.01); *A61Q 5/06* (2013.01); *A61Q 9/02* (2013.01); *A61Q 19/00* (2013.01); *C08F 120/58* (2013.01); *C08F 220/58* (2013.01); *C08F 222/385* (2013.01)

(58) Field of Classification Search
None
See application file for complete search history.

(56) References Cited

U.S. PATENT DOCUMENTS 4,771,105 A    9/1988  Shirai et al.
4,822,848 A    4/1989  Ito et al.
(Continued)

FOREIGN PATENT DOCUMENTS

| | | |
|---|---|---|
| JP | S-57-202309 | 12/1982 |
| JP | 2009-175875 | 7/1997 |
| WO | WO-99/64563 | 12/1999 |

OTHER PUBLICATIONS

J. G. Cannon, Burger's Medicinal Chemistry and Drug Discovery, Fifth Edition, vol. I: Principles and Practice, Wiley-Interscience 1995, pp. 783-802, 784.*

(Continued)

*Primary Examiner* — Jianfeng Song
(74) *Attorney, Agent, or Firm* — Foley & Lardner LLP

(57) ABSTRACT

Embodiments presented herein relate to acrylamide derivatives and uses thereof. Examples of such derivatives include acrylamide pyranose and other acrylamides that have other carbohydrate or 5 or 6 membered rings attached thereto. The compositions can be used for a variety of purposes, e.g., cosmetics, construction, scaffold materials, hydrogels, food additives, baby diapers, tubing sieves, etc.

12 Claims, 5 Drawing Sheets

(51) Int. Cl.
*A61Q 9/02* (2006.01)
*A61Q 19/00* (2006.01)

(56) References Cited

U.S. PATENT DOCUMENTS

| | | | |
|---|---|---|---|
| 6,410,668 B1 | 6/2002 | Chiari | |
| 6,488,901 B1 | 12/2002 | Schmidt et al. | |
| 6,552,103 B1 | 4/2003 | Bertozzi et al. | |
| 2002/0111281 A1 | 8/2002 | Vishnupad | |
| 2002/0128346 A1 | 9/2002 | Domschke et al. | |
| 2002/0150688 A1 | 10/2002 | Knight et al. | |
| 2004/0058006 A1* | 3/2004 | Barry | C08B 37/0021 424/489 |
| 2006/0113080 A1 | 6/2006 | Nguyen et al. | |
| 2007/0107638 A1 | 5/2007 | Chun et al. | |
| 2008/0057206 A1 | 3/2008 | Igo et al. | |
| 2008/0066509 A1 | 3/2008 | Turley | |
| 2008/0281064 A1 | 11/2008 | Chiron et al. | |
| 2009/0018300 A1* | 1/2009 | Bloom | C08G 61/12 527/102 |
| 2010/0003236 A1 | 1/2010 | Dalko et al. | |
| 2010/0291055 A1 | 11/2010 | Athanasiadis et al. | |
| 2011/0275577 A1 | 11/2011 | Priebe et al. | |
| 2011/0282048 A1 | 11/2011 | Brumer et al. | |

OTHER PUBLICATIONS

Sheridan, The most Common Chemical Replacement in Drug-like Compounds, J. Chem. Inf. Comput. Sci., 2002, vol. 42, pp. 103-108.*
Bahulekar et al., "Polyacrylamide containing sugar residues: synthesis, characterization and cell compatibility studies" Carbohydrate Polymers, 1998, vol. 37, No. 1, pp. 71-78.
Bahulekar, R. et al., "Polyacrylamides containing sugar residues: synthesis, characterization and hepatocyte attachment studies," Biotechnology Techniques, Oct. 1998, vol. 12, No. 10, pp. 721-724.
Bird, T.P., et al, "Polyamides Containing Carbohydrate Residues," Journal of the Chemical Society, 1963, pp. 3389-3391.
Bird, T.P., et al., "Preparation and derivatives of poly-(6-O-methacryloyl-D-galactose) and poly-(6-O-acryloyl-D-galactose)," Journal of the Chemical Society (C), vol. 21, 1966, pp. 1913-1918.
Black, W. A. P., et al., "6-O-Methacryloyl-D-galactose: a reactive, water-soluble monomer," Die Makromolekulare Chemie, vol. 117, No. 2817, 1968, pp. 210-214.
Hill, et al., "Carbohydrate Protein Conjugates (CPC): The Design of New Materials to Stabilize Enzymes," Mat. Res. Symp. Proc., vol. 218, 1991, pp. 7-15.
International Search Report and Written Opinion for PCT/US2012/063240, mailed on Jan. 22, 2013, 9 pp.
International Search Report and Written Opinion for PCT/US12/63211, mailed on Mar. 15, 2013.
International Search Report and Written Opinion for PCT/US2012/063261, mailed on Jan. 22, 2013.
International Search Report and Written Opinion for PCT/US12/67765 mailed Feb. 26, 2013.
International Search Report and Written Opinion for PCT/US2012/067782 mailed Feb. 5, 2013.
Paterson, et al., "Carbohydrate-Based Crosslinking Agents: Potential Use in Hydrogels," Journal of Polymer Science Part A: Polymer Chemistry 2011, vol. 49, pp. 4312-4315.
Petrie, E. M., "Biodegradable Polymers in Adhesive Systems," ASI, accessed at https://web.archive.org/web/20120822220909/http://www.adhesivesmag.com/articles/print/biodegradable-polymers-in-adhesive-systems, Jun. 1, 2007, 6 pages.
Rodger, S.L., et al, "High Strength Cement Pastes," Journal of Materials Science, vol. 20, Aug. 1985, pp. 2853-2860.
Suo, A., et al., "Synthesis and properties of carboxymethyl cellulose-graft-poly(acrylic acid-co-acrylamide) as a novel cellulose-based superabsorbent," Journal of Applied Polymer Science, vol. 103, Issue 3, Feb. 5, 2007, pp. 1382-1388.
Wang, Y., et al., "Fabrication and characterization of a PAM modified PHBV/BG scaffold," Chinese Science Bulletin, vol. 54, No. 17, 2009, pp. 2940-2946.
Zhang, Y. et al., "Stimuli-responsive copolymers of n-isopropyl acrylamide with enhanced longevity in water for micro- and nanofluidics, drug delivery and non-woven applications," 2009, J. Mater. Chem. 19, pp. 4732-4739.
Badey, B., et al., "Radically initiated polymerization of a methacryloylamido-terminated saccharide, 1. Monomer synthesis, homopolymerization and characterizations," Macromolecular Chemistry and Physics, vol. 197, Issue 11, pp. 3711-3728 (Nov. 1996).
Badey, B., et al., "Radically initiated polymerization of a methacryloylamido-terminated saccharide, 2. Copolymerization with 2-hydroxyethyl methacrylate," Macromolecular Chemistry and Physics, vol. 198, Issue 4, pp. 945-957 (Apr. 1997).

* cited by examiner

ACRYLAMIDE DERIVATIVES

CROSS-REFERENCE TO RELATED APPLICATION

This application is a national stage application under 35 of U.S.C. §371 of International Application No. PCT/US2012/063211, filed on Nov. 2, 2012, the contents of which are incorporated herein by reference in their entirety for any and all purposes.

TECHNICAL FIELD

Embodiments provided herein generally relate to acrylamide derivatives.

BACKGROUND

Acrylamide is a widely used chemical compound. It is derived from hydrating acrylonitrile. Its cousin methacrylamide is derived from acetone and hydrogen cyanide. The two vinyl amides are widely used across a number of industries ranging from agriculture, food, construction, adhesives, biotech, and medical.

SUMMARY

Provided herein are acrylamide derivatives, polymers thereof, and uses thereof.

In some embodiment, various compositions are provided. In some embodiments, the compositions can be cosmetic and can include a polymer and at least one cosmetic additive. The polymer can include one or more cross-linked monomer units. The cross-linked monomer units can be represented by Formula I:

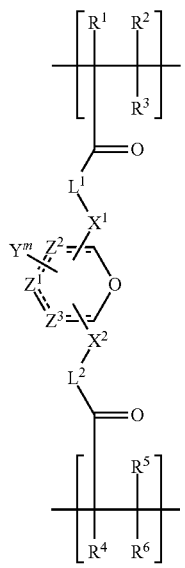

wherein, $X^1$ is a bond or $-C_{1-6}$ alkylene-; $X^2$ is a bond or $-C_{1-6}$ alkylene-; $L^1$ is —NH—, S, or O; $L^2$ is —NH—, S, or O; and each $Y^m$ is independently hydrogen, hydroxy, saturated $C_1$-$C_{24}$ alkyl, unsaturated $C_2$-$C_{24}$ alkenyl, $C_2$-$C_{24}$ alkynyl, —NR$^A$R$^B$, —NR$^A$C(O)R$^B$, —R$^C$NR$^A$R$^B$, —R$^C$NR$^A$C(O)R$^B$, —C(O)NR$^A$R$^B$, —OC(O)NR$^A$R$^B$, —C(O)R$^A$, —R$^C$C(O)R$^A$, —R$^C$OC(O)R$^A$, —C(O)OR$^A$, —R$^C$C(O)OR$^A$, —OR$^A$, —R$^C$OR$^A$, —SR$^A$, —R$^C$SR$^A$, —S(O)$_q$, —S(O)$_q$R$^C$, —OS(O)$_q$, —NS(O)$_q$, —NS(O)$_q$R$^C$, —P(O)$_q$R$^C$, —OP(O)$_q$, —NP(O)$_q$, —NP(O)$_q$R$^C$, or a substituted version thereof, wherein each $R^A$ and $R^B$ is independently hydrogen, $C_1$-$C_6$ alkyl, unsaturated $C_2$-$C_6$ alkenyl, and $C_2$-$C_6$ alkynyl, each $R^C$ is a bond, or $-C_{1-6}$ alkylene-, wherein each q is independently one, two, or three, and m is an integer from 0 to 18; $Z^1$, $Z^2$, and $Z^3$ are each independently a single bond, a double bond, —CH$_2$—, —CH(OH)—, —CH═, —CH$_2$—CH$_2$—, ═CH—CH$_2$—, ═CH—CH═, —CH═CH—, —CH$_2$—CH$_2$—CH$_2$—, ═CH—CH$_2$—CH$_2$—, ═CH—CH$_2$—CH═, ═CH—CH═CH—, or —CH═CH$_2$—CH$_2$— wherein each of $Z^1$, $Z^2$, and $Z^3$ is optionally substituted with one, two, three or four of $Y^m$, and wherein each of $Z^1$, $Z^2$, and $Z^3$ is optionally substituted with $X^1$ or $X^2$; $R^1$, $R^2$, $R^3$, $R^4$, $R^5$, and $R^6$ are each optionally substituted and independently are hydrogen, $C_1$-$C_{24}$ alkyl, unsaturated $C_2$-$C_{24}$ alkenyl or $C_2$-$C_{24}$ alkynyl, and each ═══ is a double bond or a single bond.

In some embodiments, a cosmetic composition is provided. The composition can include a polymer and at least one cosmetic additive. The composition can include less than about 0.2% by weight of acrylamide monomer. The polymer can include a monomer unit represented by Formula VI:

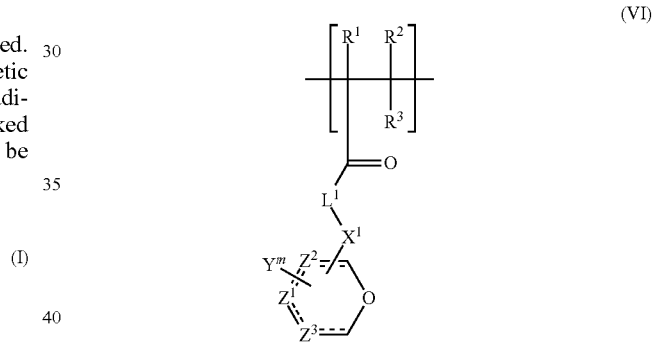

wherein, $X^1$ is a bond or $-C_{1-6}$ alkylene-; $L^1$ is —NH—, S, or O; and each $Y^m$ is independently hydrogen, hydroxy, saturated $C_1$-$C_{24}$ alkyl, unsaturated $C_2$-$C_{24}$ alkenyl, $C_2$-$C_{24}$ alkynyl, —NR$^A$R$^B$, —NR$^A$C(O)R$^B$, —R$^C$NR$^A$R$^B$, —R$^C$NR$^A$C(O)R$^B$, —C(O)NR$^A$R$^B$, —OC(O)NR$^A$R$^B$, —C(O)R$^A$, —R$^C$C(O)R$^A$, —R$^C$OC(O)R$^A$, —C(O)OR$^A$, —R$^C$C(O)OR$^A$, —OR$^A$, —R$^C$OR$^A$, —SR$^A$, —R$^C$SR$^A$, —S(O), —S(O)R$^C$, —OS(O)$_x$, —NS(O)$_x$, —NS(O)$_x$R$^C$, —P(O)$_x$R$^C$, —OP(O)$_x$, —NP(O)$_x$, —NP(O)$_x$R$^C$, or a substituted version thereof, wherein each $R^A$ and $R^B$ is independently hydrogen, $C_1$-$C_6$ alkyl, unsaturated $C_2$-$C_6$ alkenyl, or $C_2$-$C_6$ alkynyl, each $R^C$ is a bond, or $-C_{1-6}$ alkylene-, wherein each x is independently one, two, or three, and m is an integer from 0 to 19; $Z^1$, $Z^2$, and $Z^3$ are each independently a single bond, a double bond, —CH$_2$—, —CH(OH)—, —CH═, —CH$_2$—CH$_2$—, ═CH—CH$_2$—, ═CH—CH═, —CH═CH—, —CH$_2$—CH$_2$—CH$_2$—, ═CH—CH$_2$—CH$_2$—, ═CH—CH$_2$—CH═, ═CH—CH═CH—, or —CH═CH$_2$—CH$_2$— wherein each of $Z^1$, $Z^2$, and $Z^3$ is optionally substituted with one, two, three or four of $Y^m$, and wherein each of $Z^1$, $Z^2$, and $Z^3$ is optionally substituted with $X^1$; $R^1$, $R^2$, and $R^3$, are each independently hydrogen, $C_1$-$C_{24}$ alkyl, unsaturated $C_2$-$C_{24}$ alkenyl $C_2$-$C_{24}$ alkynyl, or a substituted version thereof; and each ═══ is a double bond or a single bond.

In some embodiments, a compound represented by Formula XI:

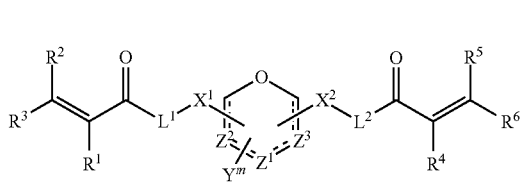

(XI)

wherein, $X^1$ is a bond or $—C_{1-6}$ alkylene-; $X^2$ is a bond or $—C_{1-6}$ alkylene-; $L^1$ is —NH—, S, or O; $L^2$ is —NH—, S, or O; and each $Y^m$ is independently hydrogen, hydroxy, saturated $C_1$-$C_{24}$ alkyl, unsaturated $C_2$-$C_{24}$ alkenyl, $C_2$-$C_{24}$ alkynyl, $—NR^AR^B$, $—NR^AC(O)R^B$, $—R^CNR^AR^B$, $—R^CN$-$R^AC(O)R^B$, $—C(O)NR^AR^B$, $—OC(O)NR^AR^B$, $—C(O)R^A$, $—R^CC(O)R^A$, $—R^COC(O)R^A$, $—C(O)OR^A$, $—R^CC(O)OR^A$, $—OR^A$, $—R^COR^A$, $—SR^A$, $—R^CSR^A$, $—S(O)_q$, $—S(O)_qR^C$, $—OS(O)_q$, $—NS(O)_q$, $—NS(O)_qR^C$, $—P(O)_qR^C$, $—OP(O)_q$, $—NP(O)_q$, $—NP(O)_qR^C$, or a substituted version thereof, wherein each $R^A$ and $R^B$ is independently hydrogen, $C_1$-$C_6$ alkyl, unsaturated $C_2$-$C_6$ alkenyl, or $C_2$-$C_6$ alkynyl, each $R^C$ is a bond, or $—C_{1-6}$ alkylene-, wherein each q is independently one, two, or three, and m is an integer 0 to 18; $Z^1$, $Z^2$, and $Z^3$ are each independently a single bond, a double bond, —CH$_2$—, —CH(OH)—, —CH=, —CH$_2$—CH$_2$—, =CH—CH$_2$—, =CH—CH=, —CH=CH—, —CH$_2$—CH$_2$—CH$_2$—, =CH—CH$_2$—CH$_2$—, =CH—CH$_2$—CH=, =CH—CH=CH—, or —CH=CH$_2$—CH$_2$— wherein each of $Z^1$, $Z^2$, and $Z^3$ is optionally substituted with one, two, three or four of $Y^m$, and wherein each of $Z^1$, $Z^2$, and $Z^3$ is optionally substituted with $X^1$ or $X^2$; $R^1$, $R^2$, $R^3$, $R^4$, $R^5$, and $R^6$ are each independently hydrogen, $C_1$-$C_{24}$ alkyl, unsaturated $C_2$-$C_{24}$ alkenyl, $C_2$-$C_{24}$ alkynyl, or a substituted version thereof; and each ══ is a double bond or a single bond.

In some embodiments, a method of preparing a polymer is provided. In some embodiments, the method includes polymerizing one or more monomers to form a polymer. In some embodiments, the one or more monomers include a first monomer selected from a monomer represented by Formula XIV, a monomer represented by Formula XV, and combinations thereof:

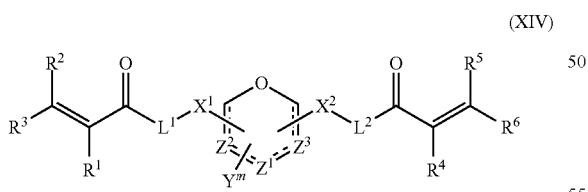

(XIV)

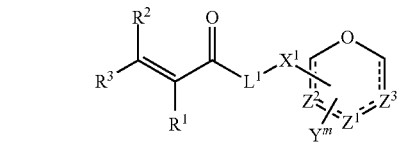

(XV)

wherein $X^1$ is a bond or $—C_{1-6}$ alkylene-; $X^2$ is a bond or $—C_{1-6}$ alkylene-; $L^1$ is —NH—, S, or O; $L^2$ is —NH—, S, or O; and each $Y^m$ is independently hydrogen, hydroxy, saturated $C_1$-$C_{24}$ alkyl, unsaturated $C_2$-$C_{24}$ alkenyl, $C_2$-$C_{24}$ alkynyl, $—NR^AR^B$, $—NR^AC(O)R^B$, $—R^CNR^AR^B$, $—R^CN$-$R^AC(O)R^B$, $—C(O)NR^AR^B$, $—OC(O)NR^AR^B$, $—C(O)R^A$, $—R^CC(O)R^A$, $—R^COC(O)R^A$, $—C(O)OR^A$, $—R^CC(O)OR^A$, $—OR^A$, $—R^COR^A$, $—SR^A$, $—R^CSR^A$, $—S(O)_q$, $—S(O)_qR^C$, $—OS(O)_q$, $—NS(O)_q$, $—NS(O)_qR^C$, $—P(O)_qR^C$, $—OP(O)_q$, $—NP(O)_q$, $—NP(O)_qR^C$, or a substituted version thereof, wherein each $R^A$ and $R^B$ is independently hydrogen, $C_1$-$C_6$ alkyl, unsaturated $C_2$-$C_6$ alkenyl, or $C_2$-$C_6$ alkynyl, each $R^C$ is a bond, or $—C_{1-6}$ alkylene-, wherein each q is independently one, two, or three, and m is an integer from 0 to 18; $Z^1$, $Z^2$, and $Z^3$ are each independently a single bond, a double bond, —CH$_2$—, —CH(OH)—, —CH=, —CH$_2$—CH$_2$—, =CH—CH$_2$—, =CH—CH=, —CH=CH—, —CH$_2$—CH$_2$—CH$_2$—, =CH—CH$_2$—CH$_2$—, =CH—CH$_2$—CH=, =CH—CH=CH—, or —CH=CH$_2$—CH$_2$— wherein each of $Z^1$, $Z^2$, and $Z^3$ is optionally substituted with one, two, three or four of $Y^m$, and wherein each of $Z^1$, $Z^2$, and $Z^3$ is optionally substituted with $X^1$ or $X^2$; and $R^1$, $R^2$, $R^3$, $R^4$, $R^5$, and $R^6$ are each independently hydrogen, $C_1$-$C_{24}$ alkyl, unsaturated $C_2$-$C_{24}$ alkenyl, $C_2$-$C_{24}$ alkynyl, or a substituted version thereof; and each ══ is a double bond or a single bond.

In some embodiments, a method of providing nutrients to skin is provided. In some embodiments, the method includes providing a cosmetic composition including a polymer; and applying the cosmetic composition to a subject's skin to provide nutrients to the subject's skin. In some embodiments, the polymer includes one or more cross-linked monomer units, and the cross-linked monomer units are represented by Formula XX:

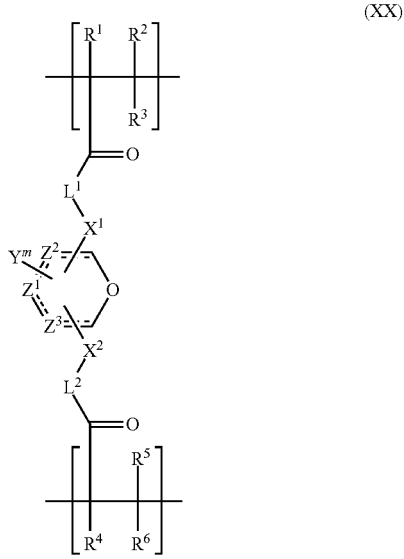

(XX)

wherein $X^1$ is a bond or $—C_{1-6}$ alkylene-; $X^2$ is a bond or $—C_{1-6}$ alkylene-; $L^1$ is —NH—, S, or O; $L^2$ is —NH—, S, or O; each $Y^m$ is independently hydrogen, hydroxy, saturated $C_1$-$C_{24}$ alkyl, unsaturated $C_2$-$C_{24}$ alkenyl, $C_2$-$C_{24}$ alkynyl, $—NR^AR^B$, $—NR^AC(O)R^B$, $—R^CNR^AR^B$, $—R^CNR^AC(O)NR^AR^B$, $—OC(O)NR^AR^B$, $—C(O)R^A$, $—R^CC(O)R^A$, $—R^COC(O)R^A$, $—C(O)OR^A$, $—R^CC(O)OR^A$, $—OR^A$, $—R^COR^A$, $—SR^A$, $—R^CSR^A$, $—S(O)_q$, $—S(O)_qR^C$, $—OS(O)_q$, $—NS(O)_q$, $—NS(O)_qR^C$, $—P(O)_qR^C$, $—OP(O)_q$, $—NP(O)_q$, $—NP(O)_qR^C$, or a substituted version thereof, wherein each $R^A$ and $R^B$ is independently hydrogen, $C_1$-$C_6$ alkyl, unsaturated $C_2$-$C_6$ alkenyl, or $C_2$-$C_6$ alkynyl, each $R^C$ is a bond, or $—C_{1-6}$ alkylene-, wherein each q is independently one, two, or three, and n is an integer from 0 to 18. In some embodiments, $Z^1$, $Z^2$, and $Z^3$ are each independently a single bond, a double bond, —$CH_2$—, —CH(OH)—, —CH=, —$CH_2$—$CH_2$—, =CH—$CH_2$—, =CH—CH=, —CH=CH—, —$CH_2$—$CH_2$—$CH_2$—, =CH—$CH_2$—$CH_2$—, =CH—$CH_2$—CH=, =CH—CH=CH—, or —CH=$CH_2$—$CH_2$— wherein each of $Z^1$, $Z^2$, and $Z^3$ is optionally substituted with one, two, three or four of $Y^m$, and wherein each of $Z^1$, $Z^2$, and $Z^3$ is optionally substituted with $X^1$ or $X^2$; $R^1$, $R^2$, $R^3$, $R^4$, $R^5$, and $R^6$ are each independently hydrogen, $C_1$-$C_{24}$ alkyl, unsaturated $C_2$-$C_{24}$ alkenyl, $C_2$-$C_{24}$ alkynyl, or a substituted version thereof; and each ==== is a double bond or a single bond.

In some embodiments, a method of providing nutrients to skin is provided. In some embodiments, the method includes providing a cosmetic composition including a polymer, wherein the composition includes less than about 0.2% by weight of acrylamide, and applying the cosmetic composition to a subject's skin to provide one or more nutrients to the subject's skin. In some embodiments, the polymer includes one or more monomer units represented by Formula XXIII:

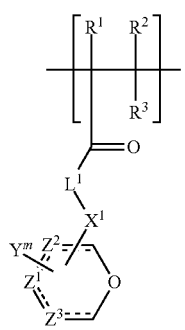

(XXIII)

wherein, $X^1$ is a bond or —$C_{1-6}$ alkylene-; $L^1$ is —NH—, S, or O; and each $Y^m$ is independently hydrogen, hydroxy, saturated $C_1$-$C_{24}$ alkyl, unsaturated $C_2$-$C_{24}$ alkenyl, $C_2$-$C_{24}$ alkynyl, —$NR^AR^B$, —$NR^AC(O)R^B$, —$R^CNR^AR^B$, —$R^CN$-$R^AC(O)R^B$, —$C(O)NR^AR^B$, —$OC(O)NR^AR^B$, —$C(O)R^A$, —$R^CC(O)R^A$, —$R^COC(O)R^A$, —$C(O)OR^A$, —$R^CC(O)OR^A$, —$OR^A$, —$R^COR^A$, —$SR^A$, —$R^CSR^A$, —$S(O)_q$, —$S(O)_qR^C$, —$OS(O)_q$, —$NS(O)_q$, —$NS(O)_qR^C$, —$P(O)_q$ $R^C$, —$OP(O)_q$, —$NP(O)_q$, —$NP(O)_qR^C$, or a substituted version thereof, wherein each $R^A$ and $R^B$ is independently hydrogen, $C_1$-$C_6$ alkyl, unsaturated $C_2$-$C_6$ alkenyl, or $C_2$-$C_6$ alkynyl, each $R^C$ is a bond, or —$C_{1-6}$ alkylene-, wherein each q is independently one, two, or three, and n is an integer from 0 to 19. In some embodiments, $Z^1$, $Z^2$, and $Z^3$ are each independently a single bond, a double bond, —$CH_2$—, —CH(OH)—, —CH=, —$CH_2$—$CH_2$—, =CH—$CH_2$—, =CH—CH=, —CH=CH—, —$CH_2$—$CH_2$—$CH_2$—, =CH—$CH_2$—$CH_2$—, =CH—$CH_2$—CH=, =CH—CH=CH—, or —CH=$CH_2$—$CH_2$—; wherein each of $Z^1$, $Z^2$, and $Z^3$ is optionally substituted with one, two, three or four of $Y^m$, and wherein each of $Z^1$, $Z^2$, and $Z^3$ is optionally substituted with $X^1$ or $X^2$; $R^1$ and $R^3$, are each independently hydrogen, $C_1$-$C_{24}$ alkyl, unsaturated $C_2$-$C_{24}$ alkenyl, $C_2$-$C_{24}$ alkynyl, or a substituted version thereof; and each ==== is a double bond or a single bond.

In some embodiments, a polymer including one or more cross-linked monomer units is provided. In some embodiments, the cross-linked monomer units are represented by Formula XXVI:

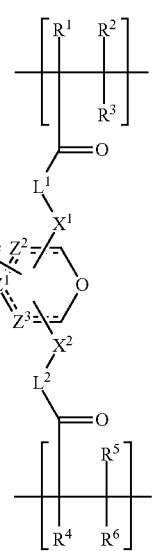

(XXVI)

wherein, $X^1$ is a bond or —$C_{1-6}$ alkylene-; $X^2$ is a bond or —$C_{1-6}$ alkylene-; $L^1$ is —NH—, S, or O; $L^2$ is —NH—, S, or O; and each $Y^m$ is independently hydrogen, hydroxy, saturated $C_1$-$C_{24}$ alkyl, unsaturated $C_2$-$C_{24}$ alkenyl, $C_2$-$C_{24}$ alkynyl, —$NR^AR^B$, —$NR^AC(O)R^B$, —$R^CNR^AR^B$, —$R^CN$-$R^AC(O)R^B$, —$C(O)NR^AR^B$, —$OC(O)NR^AR^B$, —$C(O)R^A$, —$R^CC(O)R^A$, —$R^COC(O)R^A$, —$C(O)OR^A$, —$R^CC(O)OR^A$, —$OR^A$, —$R^COR^A$, —$SR^A$, —$R^CSR^A$, —$S(O)_q$, —$S(O)_qR^C$, —$OS(O)_q$, —$NS(O)_q$, —$NS(O)_qR^C$, —$P(O)_q$ $R^C$, —$OP(O)_q$, —$NP(O)_q$, —$NP(O)_qR^C$, or a substituted version thereof, wherein each $R^A$ and $R^B$ is independently hydrogen, $C_1$-$C_6$ alkyl, unsaturated $C_2$-$C_6$ alkenyl, or $C_2$-$C_6$ alkynyl, each RC is a bond, or —$C_{1-6}$ alkylene-, wherein each q is independently one, two, or three, and m is an integer from 0 to 18. In some embodiments, $Z^1$, $Z^2$, and $Z^3$ are each independently a single bond, a double bond, —$CH_2$—, —CH(OH)—, —CH=, —$CH_2$—$CH_2$—, =CH—$CH_2$—, =CH—CH=, —CH=CH—, —$CH_2$—$CH_2$—$CH_2$—, =CH—$CH_2$—$CH_2$—, =CH—$CH_2$—CH=, =CH—CH=CH—, or —CH=$CH_2$—$CH_2$— wherein each of $Z^1$, $Z^2$, and $Z^3$ is optionally substituted with one, two, three or four of Ym, and wherein each of $Z^1$, $Z^2$, and $Z^3$ is optionally substituted with $X^1$ or $X^2$. In some embodiments, $R^1$, $R^2$, $R^3$, $R^4$, $R^5$, and $R^6$ are each independently hydrogen, $C_1$-$C_{24}$ alkyl, unsaturated $C_2$-$C_{24}$ alkenyl, $C_2$-$C_{24}$ alkynyl, or a substituted version thereof; and each ==== is a double bond or a single bond.

In some embodiments, a polymer is provided. In some embodiments, the polymer includes a monomer unit represented by Formula XXIX:

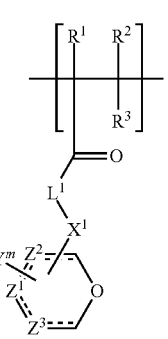

(XXIX)

wherein, $X^1$ is a bond or $-C_{1-6}$ alkylene-; $L^1$ is —NH—, S, or O; and each $Y^m$ is independently hydrogen, hydroxy, saturated $C_1$-$C_{24}$ alkyl, unsaturated $C_2$-$C_{24}$ alkenyl, $C_2$-$C_{24}$ alkynyl, $-NR^AR^B$, $-NR^AC(O)R^B$, $-R^CNR^AR^B$, $-R^CNR^AC(O)R^B$, $-C(O)NR^AR^B$, $-OC(O)NR^AR^B$, $-C(O)R^A$, $-R^CC(O)R^A$, $-R^COC(O)R^A$, $-C(O)OR^A$, $-R^CC(O)OR^A$, $-OR^A$, $-R^COR^A$, $-SR^A$, $-R^CSR^A$, $-S(O)_x$, $-S(O)_xR^C$, $-OS(O)_x$, $-NS(O)_x$, $-NS(O)_xR^C$, $-P(O)_xR^C$, $-OP(O)_x$, $-NP(O)_x$, $-NP(O)_xR^C$, or a substituted version thereof, wherein each $R^A$ and $R^B$ is independently hydrogen, $C_1$-$C_6$ alkyl, unsaturated $C_2$-$C_6$ alkenyl, or $C_2$-$C_6$ alkynyl, each $R^C$ is a bond, or $-C_{1-6}$ alkylene-, wherein each x is independently one, two, or three, and m is an integer from 0 to 19. In some embodiments, $Z^1$, $Z^2$, and $Z^3$ are each independently a single bond, a double bond, $-CH_2-$, $-CH(OH)-$, $-CH_2-CH_2-$, $=CH-CH_2-$, $=CH-CH=$, $-CH=CH-$, $-CH_2-CH_2-CH_2-$, $=CH-CH_2-CH_2-$, $=CH-CH_2-CH=$, $=CH-CH=CH-$, or $-CH=CH_2-CH_2-$ wherein each of $Z^1$, $Z^2$, and $Z^3$ is optionally substituted with one, two, three or four of $Y^m$, and wherein each of $Z^1$, $Z^2$, and $Z^3$ is optionally substituted with $X^1$; $R^1$, $R^2$, and $R^3$, are each independently hydrogen, $C_1$-$C_{24}$ alkyl, unsaturated $C_2$-$C_{24}$ alkenyl, $C_2$-$C_{24}$ alkynyl, or a substituted version thereof; and each ═══ is a double bond or a single bond.

In some embodiments, a cosmetic composition is provided. In some embodiments, the composition includes at least one of a pyranose polyacrylamide polymer or a pyranose polymethacrylamide polymer and at least one cosmetic additive.

In some embodiments, a method of providing nutrients to skin is provided. In some embodiments, the method includes providing a cosmetic composition including a pyranose polyacrylamide polymer or a pyranose polymethacrylamide polymer; and at least one cosmetic additive. In some embodiments, the composition includes less than about 0.2% by weight of acrylamide. In some embodiments, the method further includes applying the cosmetic composition to a subject's skin to provide nutrients to the subject's skin.

The foregoing summary is illustrative only and is not intended to be in any way limiting. In addition to the illustrative aspects, embodiments, and features described above, further aspects, embodiments, and features will become apparent by reference to the drawings and the following detailed description.

DETAILED DESCRIPTION

Figure 1:
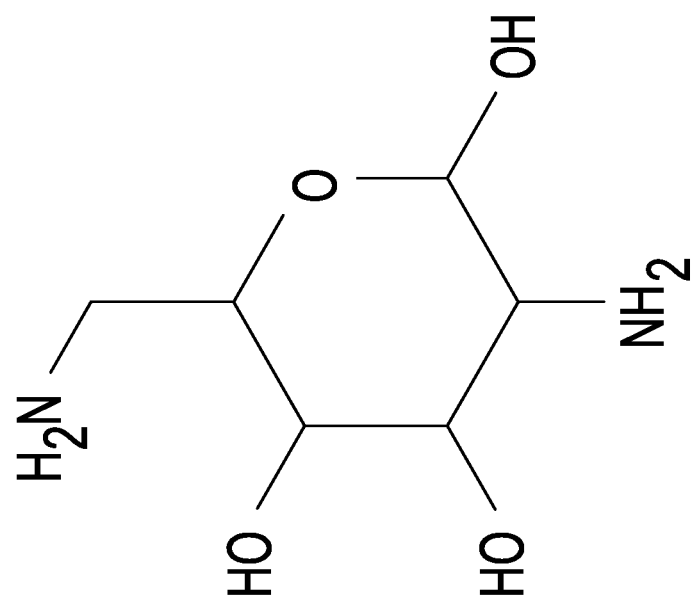
FIG. 1 is a depiction of the chemical structures of some embodiments of a mono (left) and his (right) amino pyranose. Such moieties can be attached to acrylamide (or variants and/or polymers thereof).
Figure 1:
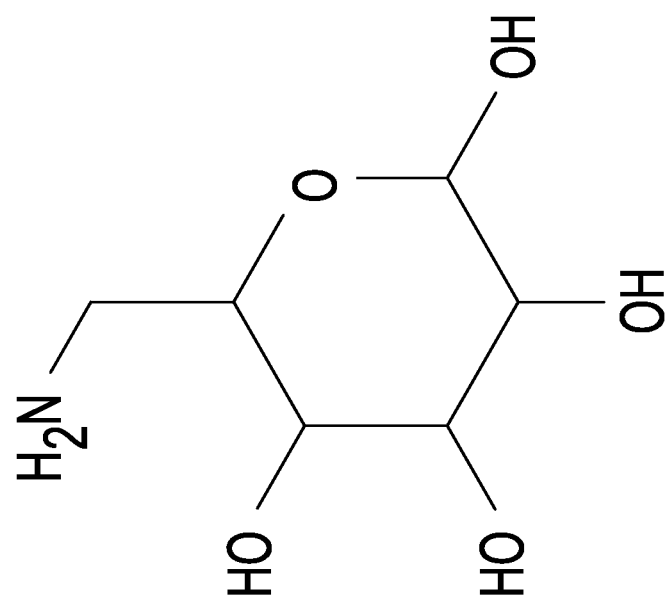

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented herein. It will be readily understood that the aspects of the present disclosure, as generally described herein, and illustrated in the Figures, can be arranged, substituted, combined, separated, and designed in a wide variety of different configurations, all of which are explicitly contemplated herein.

Provided herein are monomers, polymers, and compositions that generally relate to derivatives of acrylamide, including carbohydrate based derivatives of acrylamide.

Exemplary molecules that can serve as monomers and/or polymers include Formula XIV, and Formula XV, and combinations thereof:

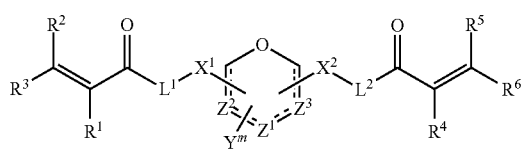

(XIV)

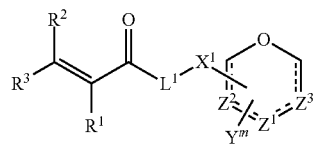

(XV)

wherein $R^1$, $R^2$, $R^3$, $L^1$, $X^1$, $Z^1$, $Z^2$, $Z^3$, $Y^m$, $X^2$, $L^2$, $R^4$, $R^5$, and $R^6$ in Formula XIV can include those options provided in more detail below, and wherein $R^1$, $R^2$, $R^3$, $L^1$, $X^1$, $Z^1$, $Z^2$, $Z^3$, and $Y^m$ can include those options provided in more detail below.

In some embodiments, the acrylamide derivative can have a carbohydrate and/or five or six membered ring attached to it, such as a pyranose moiety. In some embodiments, such arrangements can provide additional benefits and/or alternative properties over acrylamide, variants thereof, and/or polymers thereof.

In some embodiments, the degradation products from an acrylamide derivative are, or are similar to, adenosine triphospate (ATP) and/or urea, which are generally nontoxic and can readily be handled by humans and other organisms. In some embodiments, the acrylamide derivative can act as a cross-linker and allows for cross-linking of various polymers and/or other molecules. In some embodiments, even the cross-linker arrangements can also have degradation products that are also bio compatible. In some embodiments, one or more of any degradation products from the cross-linker can also be nontoxic (e.g., be, or be similar to, ATP and/or urea).

The present specification provides a brief definition section, followed by sections describing acrylamide derivatives, polymers thereof, methods of making and using, etc., followed by an examples section.

DEFINITIONS

As used herein, "alkyl" refers to a straight or branched hydrocarbon chain that includes a fully saturated (no double or triple bonds) hydrocarbon group. The alkyl group of the compounds may be designated as "$C_1$-$C_4$ alkyl" or similar designations. By way of example only, "$C_1$-$C_4$ alkyl" indicates that there are one to four carbon atoms in the alkyl chain, i.e., the alkyl chain is selected from methyl, ethyl, propyl, iso-propyl, n-butyl, iso-butyl, sec-butyl, and t-butyl. Typical alkyl groups include, but are in no way limited to, methyl, ethyl, propyl, isopropyl, butyl, isobutyl, tertiary butyl, pentyl, hexyl, and the like.

As used herein, "alkylene" refers to a straight or branched, fully saturated (no double or triple bonds) hydrocarbon tethering group that forms bonds to connect molecular fragments via their terminal carbon atoms. The alkylene group of the compounds may be designated as "—$C_1$-$C_4$ alkyl-" or similar designations. By way of example only, "—$C_1$-$C_4$ alkyl-" indicates that there are one to four carbon atoms in the alkylene chain. Examples of alkylene groups include but are not limited to methylene (—$CH_2$—), ethylene (—$CH_2CH_2$—), propylene (—$CH_2CH_2CH_2$—), dimethyl-methylene (—$CH(CH_3)_2$—), and butylene (—$CH_2CH_2CH_2CH_2$—).

As used herein, the term "hydroxyl" refers to a —OH group.

As used herein, "carboxyl" refers to "—C(=O)OH" group. As would be appreciated by the skilled artisan, a carboxyl group also includes its conjugate base.

As used herein, "substituted" refers to independent replacement of one, two, three, or more of the hydrogen atoms in the specified structure with a substituent. For example, methane substituted with one or more chlorines would include chloromethane, dichloromethane, trichloromethane, and carbon tetrachloride.

Acrylamide Derivatives

Figure 2:
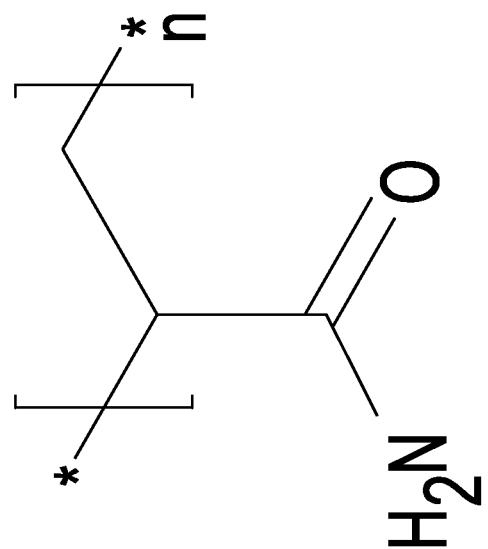
FIG. 2 is a depiction of the chemical structures of some embodiments of acrylamide (left) and poly(acrylamide) (right).
Figure 2:
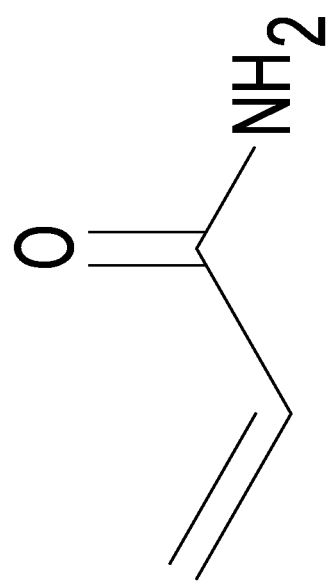
Figure 3:
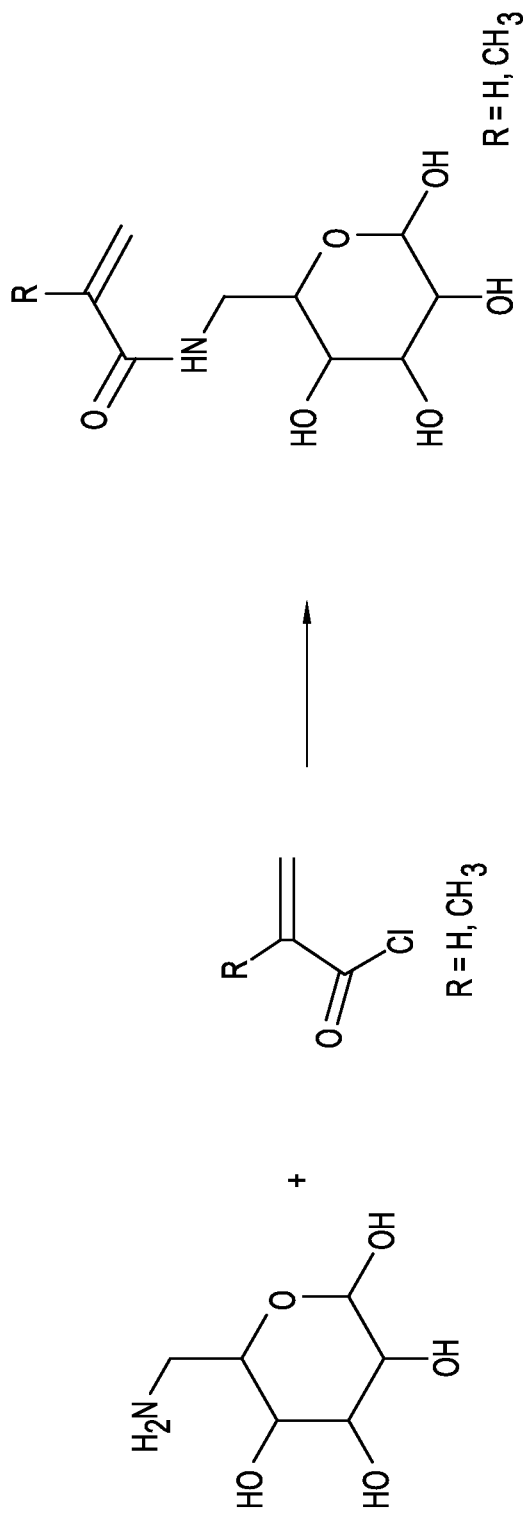
FIG. 3 is a depiction of a reaction diagram for some embodiments of the structure and synthesis of N-(3,4,5,6-tetrahydroxy-tetrahydro-pyran-2-ylmethyl)-acrylamide.

While a variety of acrylamide derivatives are disclosed herein, generally, the acrylamide derivative is one that includes a carbohydrate moiety. In some embodiments, any appropriate carbohydrate moiety can be used, including various 5 and/or 6 membered rings, such as various sugar moieties. FIG. 1 depicts some embodiments of possible carbohydrate moieties that can be employed, e.g., a root mono and bis amino pyranose. Such compounds can be combined with acrylamide (FIG. 2, left), for example, as shown in FIG. 3, to produce an acrylamide derivative of acrylamide pyranose.

Figure 4:
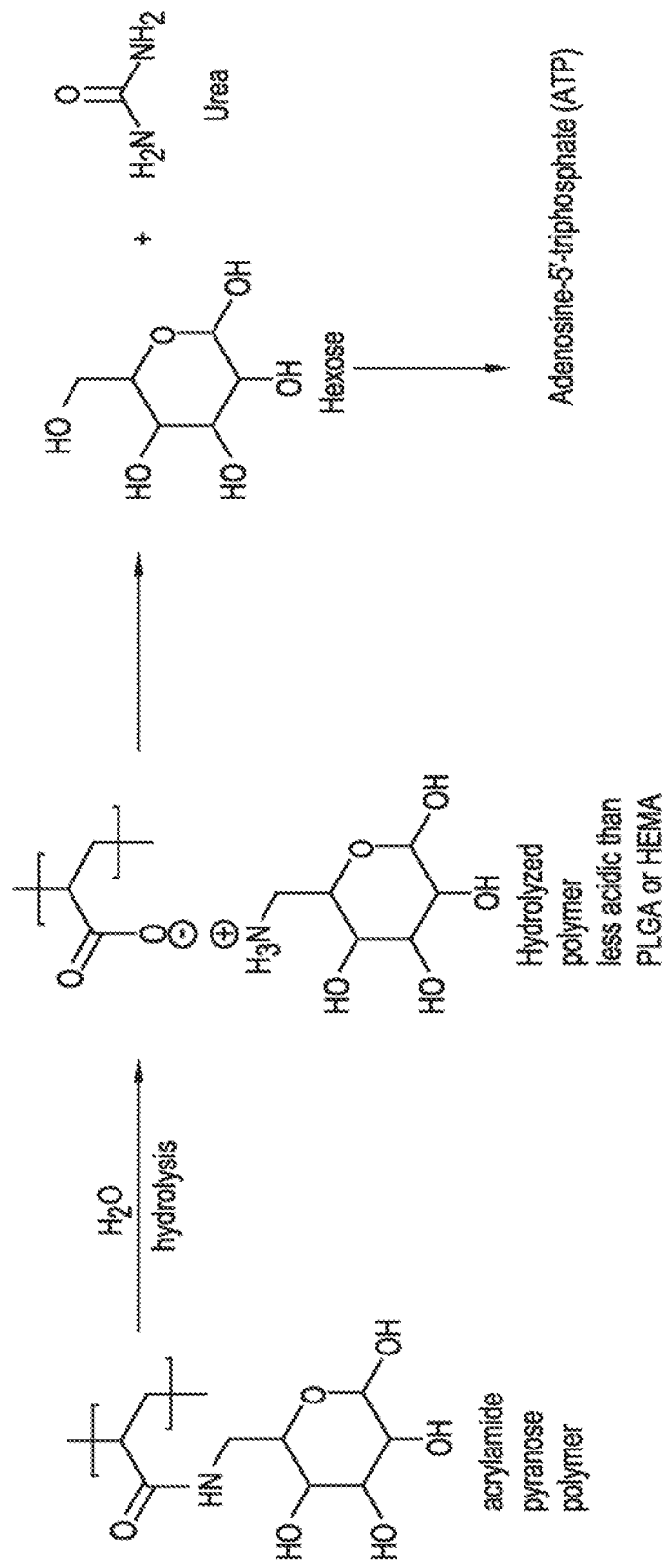
FIG. 4 is a reaction diagram for some embodiments of breakdown of polymers of acrylamide derivatives (in this case a pyranose derivative) into the products of adenosine-5'-triphosphate (ATP) and urea.

In some embodiments, the use of a carbohydrate, and/or sugar, and/or pyranose structure on an acrylamide molecule allows one to create a monomer and/or polymer product, whose natural breakdown product is, or is similar to, ATP and/or urea, natural, biological, products. For example, as shown in FIG. 4, which depicts a reaction scheme, in some embodiments, the acrylamide pyranose polymer, when broken down, results in ATP and urea, products which are not harmful (and can even be useful) for biological organisms. Thus, in some embodiments, the present compounds present an advantage over traditional acrylamide products, because the monomeric form of traditional acrylamide can be harmful, if not cancerous.

Furthermore, as noted above, in some embodiments, the acrylamide derivatives provide for a cross-linker. In some embodiments, this can be achieved by employing a carbohydrate with at least two amino groups on it (such as the his amino pyranose structure shown on the right of FIG. 1) with the acrylamide. Because of the additional amino group, the carbohydrate can serve as a cross-linker between acrylamides and/or polyacrylamides (see, e.g., the right side of FIG. 5), thereby providing for a cross-linked structure of acrylamide and/or acrylamide polymer. In some embodiments, the cross-linked structure allows for the formation of a more rigid product. In some embodiments, the composition can be cross-linked to a level so as to provide a gel or gel-like composition of greater rigidity than a typical polyacrylamide gel. In some embodiments, the cross-linker can also have or provide a degradation product similar to that of the non-cross-linking embodiments, e.g., resulting in a non-toxic degradation product, such as ATP and urea and/or variations thereof.

Due to the mechanisms of action outlined for the acrylamide derivatives provided herein, one of skill in the art will appreciate that these derivatives can be formed for a variety of acrylamide variants (and polymers thereof), such as α-methylacrylamide, α-aethylacrylamide, α-cyanoacrylamide, maleic acid mono and bis sugar amide, itaconic acid mono and his sugar amide, fumaric acid mono and bis amide. Furthermore, hydroxyl moieties can be functionalized with a variety of substituents such as alkyl, ethers, and esters containing wide variety of functional moieties. Some non-limiting examples include 3-[(3,4,5,6-tetrahydroxy-tetrahydro-pyran-2-ylmethyl)-carbamoyl]-acrylic acid, but-2-enedioic acid bis-[(3,4,5,6-tetrahydroxy-tetrahydro-pyran-2-ylmethyl)-amide], 3-[(3,4,5,6-tetrahydroxy-tetrahydro-pyran-2-ylmethyl)-carbamoyl]-but-3-enoic acid, 2-methylene-N-(3,4,5,6-tetrahydroxy-tetrahydro-pyran-2-ylmethyl)-succinamic acid, N-(3,4,5-trihydroxy-6-methoxy-tetrahydro-pyran-2-ylmethyl)-(meth)acrylamide, 2-methyl-N-(3,4,5-trihydroxy-6-methoxy-tetrahydro-pyran-2-ylmethyl)-(meth)acrylamide, 2-methylene-N-(3,4,5-trihydroxy-6-methoxy-tetrahydro-pyran-2-ylmethyl)-succinamic acid, 3-[(3,4,5-trihydroxy-6-methoxy-tetrahydro-pyran-2-ylmethyl)-carbamoyl]-acrylic acid, N-(3,4-dihydroxy-5,6-dimethoxy-tetrahydro-pyran-2-ylmethyl)-(meth)acrylamide, N-(3-hydroxy-4,5,6-trimethoxy-tetrahydro-pyran-2-ylmethyl)-acrylamide, and N-(3,4,5,6-tetramethoxy-tetrahydro-pyran-2-ylmethyl)-acrylamide. In some embodiments, the amide moieties can be moved around the sugar ring.

In some embodiments, the present acrylamide derivatives (and/or polymers thereof) can be used as an alternative to methacrylate and other acrylics. In some embodiments, one difference between acrylamides and acrylates is that oxygen does not inhibit polymerization for the acrylamides while oxygen strongly inhibits polymerization of acrylates. In some embodiments, a difference between acrylamides from acrylates is that degradation products of acrylamide are much less acidic. Thus, in some embodiments, degradation of the acrylamide carbohydrate (such as an acrylamide sugar) allows for a product that has a degradation product that is less harmful than the degradation product for a traditional polyacrylamide.

In some embodiments, any carbohydrate moiety can be attached to the acrylamide (and/or polyacrylamide). In some embodiments, any sugar moiety can be attached to the acrylamide (and/or polyacrylamide).

In some embodiments, when the acrylamide derivative has a sugar moiety attached to it, the sugar moiety is in a ring form (e.g., as shown in FIG. 1). In some embodiments, the sugar is in its linear form. Depiction of the ring form herein (including the claims) denotes the option of both the ring and linear form, unless otherwise specified. Thus, the depiction of the ring form is generic to both configurations, unless otherwise specified. It is understood that any composition can, and under most scenarios will, include species in both of the structural arrangements.

In some embodiments, a 5 or 6 membered ring can be employed as the moiety for the acrylamide derivative. In some embodiments, any six-membered ring that has five carbons and one oxygen can be used. In some embodiments, the ring can include 1, 2, 3, or 4 OH groups. In some embodiments, embodiments the ring can include 1, 2, 3, or 4 carboxylines, acetyl derivatives, sulfur, phosphors, nitrogen, ester, ketones, and/or ethers. In some embodiments, the sugar can be a decose, heptose, pentose, aldose, tetrose, glucose, galactose, fructose, and/or manose. In some embodiments, the oxygen in the ring (e.g., FIG. 3) can be substituted with a sulfur. In some embodiments, the nitrogen in the structure (FIG. 3) can be substituted with a sulfur. In some embodiments, a sulfur can be substituted at positions 2, 3, 4, 5, 6 of the molecule shown in the right side of FIG. 3. In some embodiments, any one or combination of the above can be made to any of the molecules provided herein.

While there are a wide variety of possible carbohydrates that can be attached to acrylamide to produce the acrylamide derivative, as noted above, in some embodiments, the acrylamide derivative includes two or more amino, oxygen, and/or sulfur groups, so that the acrylamide derivative can function as a cross-linker. In some embodiments, more than two amino groups can be employed. In some embodiments, tri(meth)acrylamides and/or tetra(meth)acrylamides can be employed. Some examples include N-(5,6-bis-(meth)acryloylamino-3,4-dihydroxy-tetrahydro-pyran-2-ylmethyl)-(meth)acrylamide, N-(4,5,6-tris-(meth)acryloylamino-3-hydroxy-tetrahydro-pyran-2-ylmethyl)-(meth)acrylamide, and N-(3,4,5,6-tetrakis-(meth)acryloylamino-tetrahydro-pyran-2-ylmethyl)-(meth)acrylamide.

In some embodiments, the acrylamide derivative cross-linker is represented by Formula XI:

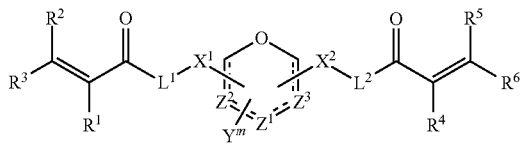

(XI)

wherein, $X^1$ is a bond or —$C_{1-6}$ alkylene-; $X^2$ is a bond or —$C_{1-6}$ alkylene-; $L^1$ is —NH—, S, or O; and $L^2$ is —NH—, S, or O. In some embodiments, each $Y^m$ is independently hydrogen, hydroxy, saturated $C_1$-$C_{24}$ alkyl, unsaturated $C_2$-$C_{24}$ alkenyl, $C_2$-$C_{24}$ alkynyl, —$NR^AR^B$, —$NR^AC(O)R^B$, —$R^CNR^AR^B$, —$R^CNR^AC(O)R^B$, —$C(O)NR^AR^B$, $OC(O)N$-$R^AR^B$, —$C(O)R^A$, —$R^CC(O)R^A$, —$R^COC(O)R^A$, —$C(O)OR^A$, —$R^CC(O)OR^A$, —$OR^A$, —$R^COR^A$, —$SR^A$, —$R^CSR^A$, —$S(O)_q$, —$S(O)_qR^C$, —$OS(O)_q$, —$NS(O)_q$, —$NS(O)_qR^C$, —$P(O)_qR^C$, —$OP(O)_q$, —$NP(O)_q$, —$NP(O)_qR^C$, or a substituted version thereof, wherein each $R^A$ and $R^B$ is independently hydrogen, $C_1$-$C_6$ alkyl, unsaturated $C_2$-$C_6$ alkenyl, or $C_2$-$C_6$ alkynyl, each $R^C$ is a bond, or —$C_{1-6}$ alkylene-, wherein each q is independently one, two, or three, and m is an integer 0 to 18; wherein, $Z^1$, $Z^2$, and $Z^3$ are each independently a single bond, a double bond, —$CH_2$—, —CH(OH)—, —CH=, —$CH_2$—$CH_2$—, =CH—$CH_2$—, =CH—CH=, —CH=CH—, —$CH_2$—$CH_2$—$CH_2$—, =CH—$CH_2$—$CH_2$—, =CH—$CH_2$—CH=, =CH—CH=CH—, or —CH=$CH_2$—$CH_2$— wherein each of $Z^1$, $Z^2$, and $Z^3$ is optionally substituted with one, two, three or four of $Y^m$, and wherein each of $Z^1$, $Z^2$, and $Z^3$ is optionally substituted with $X^1$ or $X^2$; wherein, $R^1$, $R^2$, $R^3$, $R^4$, $R^5$, and $R^6$ are each independently hydrogen, $C_1$-$C_{24}$ alkyl, unsaturated $C_2$-$C_{24}$ alkenyl, $C_2$-$C_{24}$ alkynyl, or a substituted version thereof; and wherein each ==== is a double bond or a single bond.

In some embodiments, the acrylamide derivative is one that is represented by Formulae XII or XIII:

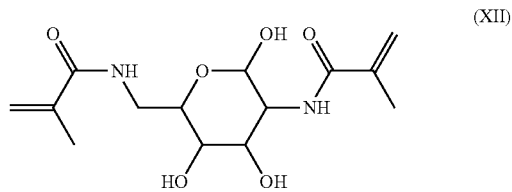

(XII)

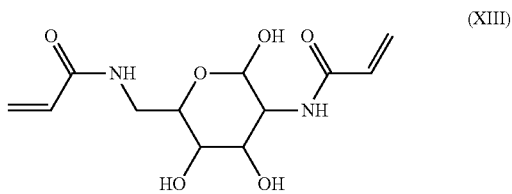

(XIII)

In some embodiments, these compounds are separate from any polymer product. In some embodiments, these molecules are monomers within a polymer. In some embodiments, these compounds are in mixtures which also include polymers and/or other monomers.

Polymers

In some embodiments, one or more of the monomers of the acrylamide derivative provided herein can be used in or to create a polymer. In some embodiments, the polymers can provide one or more of the following advantages: non-carcinogenic, lower viscosity solutions, used at high concentrations, toxic materials are not released, degradation products of acrylamides are much less acidic, elimination of inflammatory response, strong affinity for water, superior moisturizer, environmentally friendly and biodegradable, oxygen does not inhibit polymerization, and/or provides an energy source for cell growth and skin health, when compared to traditional acrylamides.

In some embodiments, any of the molecules provided herein can be used as monomer in a polymer.

In some embodiments, the polymers provided herein can be used as an alternative and/or as a supplement to a polyacrylamide polymer. For example, a polyacrylamide derivative can be used as an additive to cosmetics (e.g., as a hydrogel material) to moisturize the skin and give a better feel of the product to the consumer. Similarly, they can be used as a water absorbent polymer, capable to absorbing up to 1000 times it weight in distilled water, and 50 times it weight in 3% saline solution. In some embodiments, the acrylamide derivative will be a better water absorbent in saline.

In some embodiments, temperatures of 120 degrees Centigrade need not be employed when using the acrylamide derivative.

In some embodiments, the polymer can include any one or more of the compounds provided herein. In some embodiments, the polymer can include any one or more of the monomer units provided below.

In some embodiments, the polymer includes one or more cross-linked monomer units, wherein the cross-linked monomer units are represented by Formula XXVI:

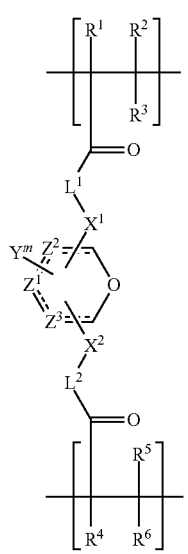

(XXVI)

wherein, $X^1$ is a bond or —$C_{1-6}$ alkylene-; $X^2$ is a bond or —$C_{1-6}$ alkylene-; $L^1$ is —NH—, S, or O; and $L^2$ is —NH—, S, or O. In some embodiments, each $Y^m$ is independently hydrogen, hydroxy, saturated $C_1$-$C_{24}$ alkyl, unsaturated $C_2$-$C_{24}$ alkenyl, $C_2$-$C_{24}$ alkynyl, —$NR^AR^B$, —$NR^AC(O)R^B$, —$R^CNR^AR^B$, —$R^CNR^AC(O)R^B$, —C(O)$NR^AR^B$, —OC(O)$NR^AR^B$, —C(O)$R^A$, —$R^CC(O)R^A$, —$R^COC(O)R^A$, —C(O)$OR^A$, —$R^CC(O)OR^A$, —$OR^A$, —$R^COR^A$, —$SR^A$, —$R^CSR^A$, —S(O)$_q$, —S(O)$_qR^C$, —OS(O)$_q$, —NS(O)$_q$, —NS(O)$_qR^C$, —P(O)$_qR^C$, —OP(O)$_q$, —NP(O)$_q$, —NP(O)$_qR^C$, or a substituted version thereof, wherein each $R^A$ and $R^B$ is independently hydrogen, $C_1$-$C_6$ alkyl, unsaturated $C_2$-$C_6$ alkenyl, or $C_2$-$C_6$ alkynyl, each $R^C$ is a bond, or alkylene-, wherein each q is independently one, two, or three, and m is an integer from 0 to 18; wherein, $Z^1$, $Z^2$, and $Z^3$ are each independently a single bond, a double bond, —CH$_2$—, —CH(OH)—, —CH=, —CH$_2$—CH$_2$—, =CH—CH$_2$—, =CH—CH=, —CH=CH—, —CH$_2$—CH$_2$—CH$_2$—, =CH—CH$_2$—CH$_2$—, =CH—CH$_2$—CH=, =CH—CH=CH—, or —CH=CH$_2$—CH$_2$— wherein each of $Z^1$, $Z^2$, and $Z^3$ is optionally substituted with one, two, three or four of $Y^m$, and wherein each of $Z^1$, $Z^2$, and $Z^3$ is optionally substituted with $X^1$ or $X^2$; wherein $R^1$, $R^2$, $R^3$, $R^4$, $R^5$, and $R^6$ are each independently hydrogen, $C_1$-$C_{24}$ alkyl, unsaturated $C_2$-$C_{24}$ alkenyl, $C_2$-$C_{24}$ alkynyl, or a substituted version thereof; and wherein each ═══ is a double bond or a single bond.

In some embodiments, the polymer does not need to include a cross-linked monomer. In some embodiments, the polymer includes a monomer unit represented by Formulae XXVII or XXVIII:

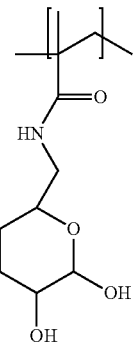

(XXVII)

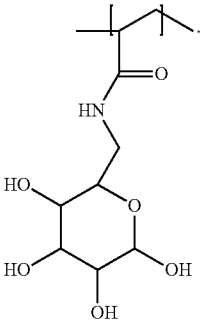

(XXVIII)

In some embodiments, a polymer including a monomer unit represented by Formula XXIX:

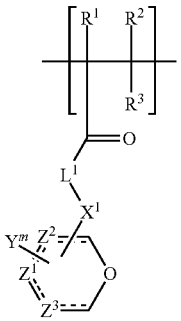

(XXIX)

wherein, $X^1$ is a bond or —$C_{1-6}$ alkylene-; and $L^1$ is —NH—, S, or O. In some embodiments, each $Y^m$ is independently hydrogen, hydroxy, saturated $C_1$-$C_{24}$ alkyl, unsaturated $C_2$-$C_{24}$ alkenyl, $C_2$-$C_{24}$ alkynyl, —$NR^AR^B$, —$NR^AC(O)R^B$, —$R^CNR^AR^B$, —$R^CNR^AC(O)R^B$, —C(O)$NR^AR^B$, —OC(O)$NR^AR^B$, —C(O)$R^A$, —$R^CC(O)R^A$, —$R^COC(O)R^A$, —C(O)$OR^A$, —$R^CC(O)OR^A$, —$OR^A$, —$R^COR^A$, —$SR^A$, —$R^CSR^A$, —S(O), —S(O)$R^C$, —OS(O)$_x$, —NS(O)$_x$, —NS(O)$_xR^C$, —P(O)$_xR^C$, —OP(O)$_x$, —NP(O)$_x$, —NP(O)$_xR^C$, or a substituted version thereof, wherein each $R^A$ and $R^B$ is independently hydrogen, $C_1$-$C_6$ alkyl, unsaturated $C_2$-$C_6$ alkenyl, or $C_2$-$C_6$ alkynyl, each $R^C$ is a bond, or —$C_{1-6}$ alkylene-, wherein each x is independently one, two, or three, and m is an integer from 0 to 19; wherein, $Z^1$, $Z^2$, and $Z^3$ are each independently a single bond, a double bond, —CH$_2$—, —CH(OH)—, —CH=, —CH$_2$—CH$_2$—, =CH—CH$_2$—, =CH—CH=, —CH=CH—, —CH$_2$—CH$_2$—CH$_2$—, =CH—CH$_2$—CH$_2$—, =CH—CH$_2$—CH=, =CH—CH=CH—, or —CH=CH$_2$—CH$_2$— wherein each of $Z^1$, $Z^2$, and $Z^3$ is optionally substituted with one, two, three or four of $Y^m$, and wherein each of $Z^1$, $Z^2$, and $Z^3$ is optionally substituted with $X^1$; wherein, $R^1$, $R^2$, and $R^3$, are each independently hydrogen, $C_1$-$C_{24}$ alkyl, unsaturated $C_2$-$C_{24}$ alkenyl, $C_2$-$C_{24}$ alkynyl, or a substituted version thereof, and wherein each ══ is a double bond or a single bond.

In some embodiments, the polymer includes a monomer unit represented by Formula XXX or XXXI:

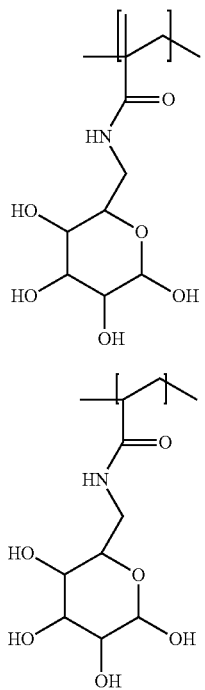

(XXX)

(XXXI)

In some embodiments, the acrylamide derivative can be used in foods, cosmetics, construction, and/or adhesives. In some embodiments, the acrylamide derivative can be used to reduce an amount of a non-derivative acrylamide to under an average of 0.03% of a composition by weight, e.g., less than 0.02, 0.01, 0.001, or 0.0001%. In some embodiments, the acrylamide derivative can be used to reduce non-derivative acrylamide (e.g., the acrylamide shown in FIG. 2) levels in a product to 5 ppm acrylamide residues or less, for example, in cosmetics and personal care products, e.g., less than 5, 4, 3, 2, 1, 0.5, 0.1, 0.05, 0.01, 0.001, 0.0001, 0.00001, 0.000001 or less ppm.

In some embodiments, the polymer can be any size. In some embodiments, the polymer can include 2 or more monomers. In some embodiments, the polymer is about 10,000 to about 1,000,000 units in size, e.g., 10,000, 50,000, 100,000, 200,000, 300,000, 400,000, 500,000, 600,000, 700,000, 800,000, 900,000, or 1,000,000 units in size, including any range above any one of the preceding values and any range between any two of the preceding values.

Cosmetic Composition

In some embodiments, the monomers, polymers, and decomposition products provided herein can be used or be present in cosmetics and/or personal care products. In some embodiments, any acrylamide derivative can be used in the formulation of one or more product types including skin cleansers, moisturizers, lotions and creams, self tanning products, makeup, hair care and nail care products. In some embodiments, the acrylamide derivative can be used to replace and/or supplement traditional poly(acrylamide). In some embodiments, the resulting cosmetic product has less than about 0.2% acrylamide monomer in it, e.g., 0.19, 0.15, 0.1, 0.05, 0.01, 0.001, 0.0001, 0.00001% or lower of an amount of acrylamide monomer present. In some embodiments, there is no acrylamide monomer, or at least no more than is detectable.

In some embodiments, the acrylamide derivative can be used in body-care leave-on products and other cosmetic products. In some embodiments, the product will have a maximum residual acrylamide content of less than about 0.5 mg/kg, e.g., 0.4, 0.3, 0.2, 0.1, 0.05, 0.01, 0.005, 0.001, 0.0001, 0.00001 or lower, including any range between any two of the preceding values and any range beneath any one of the preceding values.

In some embodiments, the acrylamide derivative, in polymer form, exhibits excellent utility in cosmetics to make the product appear more pleasing, palatable, and attractive to the user and/or customer. In some embodiments, the product having the polymer does not have the carcinogenic affects of acrylamide due to differences in structure and behavior upon degradation.

In some embodiments, a cosmetic composition is provided and can include a pyranose polyacrylamide polymer and/or a pyranose polymethacrylamide polymer. In some embodiments, it can further include at least one cosmetic additive.

In some embodiments, the cosmetic composition includes a polymer and at least one cosmetic additive. In some embodiments, the polymer includes any one or more of the cross-linked monomer units, provided herein.

In some embodiments, the cosmetic composition can include the compound of Formula I. In some embodiments, $Z^1$ is —CH$_2$—, —CHY$^m$—, or —CY$^m$Y$^m$—. In some embodiments, $Z^2$ is —CH$_2$—, —CHY$^m$—, or —CY$^m$Y$^m$—. In some embodiments, $Z^3$ is —CH$_2$—, —CHY$^m$—, —CY$^m$Y$^m$—, or —CHX$^2$—. In some embodiments, $Z^3$ is —CHX$^2$—. In some embodiments, $Z^1$, $Z^2$, and $Z^3$ are each —CH(OH)—. In some embodiments, $L^1$ is —NH—. In some embodiments, $L^2$ is —NH—. In some embodiments, each ══ is a single bond. In some embodiments, the molecule can be that depicted in Formula II:

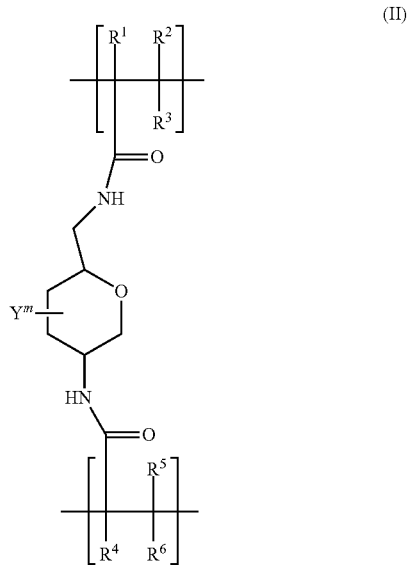

(II)

In some embodiments, the cosmetic composition can include the cross-linked monomer units represented by Formula III:

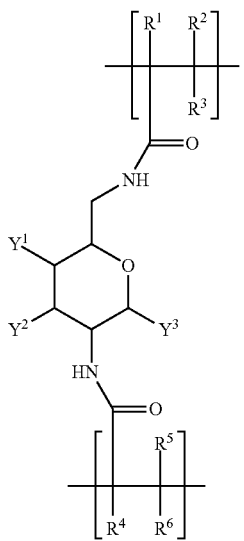

(III)

wherein $Y^1$, $Y^2$, and $Y^3$ are each independently $Y^m$; wherein $Y^1$, $Y^2$, and $Y^3$ are each hydroxyl, wherein $R^1$ is hydrogen or methyl, wherein, $R^4$ is hydrogen or methyl; wherein $R^1$ is methyl, $R^4$ is methyl, $R^3$ is hydrogen, and $R^6$ is hydrogen; and wherein $R^2$, $R^3$, $R^5$, and $R^6$ are each hydrogen. In some embodiments, the cross-linked monomer units are represented by Formula IV or V:

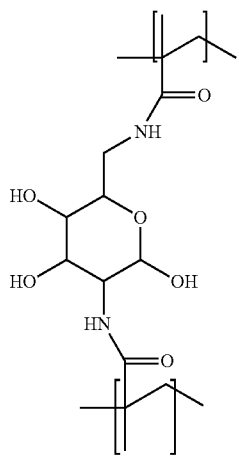

(IV)

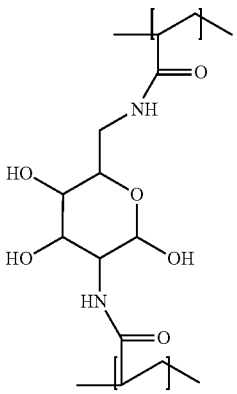

(V)

In some embodiments, the cosmetic composition need not be cross-linked or include a second nitrogen group for cross-linking. In some embodiments, the cosmetic composition can include less than about 0.2% by weight of an acrylamide monomer. In some embodiments, the polymer can include a monomer unit represented by Formula VI:

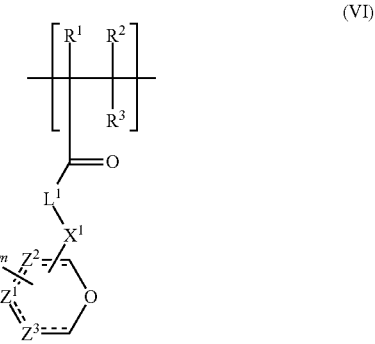

(VI)

wherein $X^1$ is a bond or —$C_{1-6}$ alkylene-; and $L^1$ is —NH—, S, or O. In some embodiments, each $Y^m$ is independently hydrogen, hydroxy, saturated $C_1$-$C_{24}$ alkyl, unsaturated $C_2$-$C_{24}$ alkenyl, $C_2$-$C_{24}$ alkynyl, —$NR^A R^B$, —$NR^A C(O)R^B$, —$R^C NR^A R^B$, —$R^C NR^A C(O)R^B$, —$C(O)NR^A R^B$, —$OC(O)NR^A R^B$, —$C(O)R^A$, —$R^C C(O)R^A$, —$R^C OC(O)R^A$, —$C(O)OR^A$, —$R^C C(O)OR^A$, —$OR^A$, —$R^C OR^A$, —$SR^A$, —$R^C SR^A$, —$S(O)_x$, —$S(O)_x R^C$, —$OS(O)_x$, —$NS(O)_x$, —$NS(O)_x R^C$, —$P(O)_x R^C$, —$OP(O)_x$, —$NP(O)_x$, —$NP(O)_x R^C$, or a substituted version thereof, wherein each $R^A$ and $R^B$ is independently hydrogen, $C_1$-$C_6$ alkyl, unsaturated $C_2$-$C_6$ alkenyl, or $C_2$-$C_6$ alkynyl, each $R^C$ is a bond, or —$C_{1-6}$ alkylene-, wherein each x is independently one, two, or three, and m is an integer from 0 to 19. In some embodiments, $Z^1$, $Z^2$, and $Z^3$ are each independently a single bond, a double bond, —$CH_2$—, —$CH(OH)$—, —$CH=$, —$CH_2$—$CH_2$—, =$CH$—$CH_2$—, =$CH$—$CH=$, —$CH=CH$—, —$CH_2$—$CH_2$—$CH_2$—, =$CH$—$CH_2$—$CH_2$—, =$CH$—$CH_2$—$CH=$, =$CH$—$CH=CH$—, or —$CH=CH_2$—$CH_2$— wherein each of $Z^1$, $Z^2$, and $Z^3$ is optionally substituted with one, two, three or four of $Y^m$, and wherein each of $Z^1$, $Z^2$, and $Z^3$ is optionally substituted with $X^1$; wherein $R^1$, $R^2$, and $R^3$, are each independently hydrogen, $C_1$-$C_{24}$ alkyl, unsaturated $C_2$-$C_{24}$ alkenyl $C_2$-$C_{24}$ alkynyl, or a substituted version thereof; and wherein each ═══ is a double bond or a single bond.

In some embodiments, $Z^1$ is —CH$_2$—, —CHY$^m$—, or —CY$^m$Y$^m$—. In some embodiments, $Z^2$ is —CH$_2$—, —CHY$^m$—, or —CY$^m$Y$^m$—. In some embodiments, $Z^3$ is —CH$_2$—, —CHY$^m$—, —CY$^m$Y$^m$—, or —CHX$^2$—. In some embodiments, $Z^3$ is —CX$^2$—. In some embodiments, $Z^1$, $Z^2$, and $Z^3$ are each —CH(OH)—. In some embodiments, $L^1$ is —NH—. In some embodiments, $L^2$ is —NH—. In some embodiments, each ═══ is a single bond. In some embodiments, the monomer unit is represented by Formula VII:

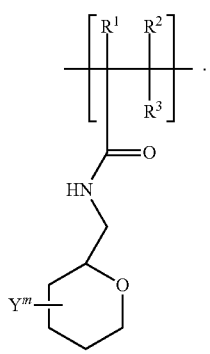

(VII)

wherein $Y^1$, $Y^2$, $Y^3$, and $Y^4$ are each independently $Y^m$. In some embodiments, the monomer unit is represented by Formula VIII:

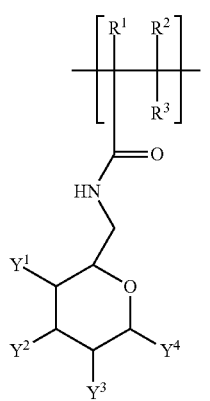

(VIII)

wherein $Y^1$, $Y^2$, $Y^3$, and $Y^4$ are each independently $Y^m$. In some embodiments, $Y^1$, $Y^2$, $Y^3$, and $Y^4$ are each hydroxy. In some embodiments, $R^1$ is hydrogen or methyl. In some embodiments, $R^2$ is hydrogen $R^3$ is hydrogen.

In some embodiments, the cosmetic composition includes less than about 1% by weight of acrylamide and methacrylamide monomer units, e.g., less than 0.9, 0.5, 0.1, 0.01, 0.001, 0.0001, 0.00001, 0.000001, or 0.0000001% by weight, including any range between any two of the preceding values and any range beneath any single value (including no detectable amount of acrylamide and/or methacrylamide).

In some embodiments, the cosmetic composition can include a polymer including a monomer unit represented by Formula IX or X:

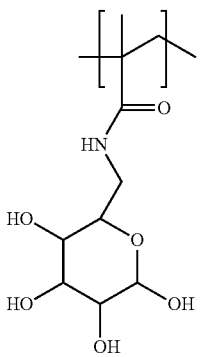

(IX)

(X)

In some embodiments, any of a variety of cosmetic additives or ingredients can be combined with any one or more of the polymers provided herein. In some embodiments, the cosmetic additive can be a GRAS ingredient ("Generally Regarded as Safe"). In some embodiments, the cosmetic additive can include one or more of the following: denatured alcohol, alkyl benzoate $C_{12}$-$C_{15}$, allantoin, alpha-isomethyl ionone, aluminum chlorohydrate, water, wax, ascorbyl palmitate, butane, butyrospermum parkii, hydroxyethyl-cellulose, hydroxypropyl-cellulose, isobutane, isopentane, propane, sodium hydroxide, castor oil, dye, triethanolamine, purified water, sodium lauryl sulfate (from coconut oil), sodium laureth sulfate (from coconut oil), olefin sulfonate, cocamidopropyl betaine (from coconut oil), decyl glucoside, citric acid, paraben, emulsifying wax, beeswax, vegetable glycerin, oat bran, passion fruit juice, red rose water, raspberry extract, yucca herbal extract, aloe vera leaf gel, tea tree oil, peppermint leaf oil, spearmint leaf oil, wintergreen leaf oil, lavender oil, cinnamon leaf oil, lemon Peel oil, valencia orange peel oil, pink grapefruit peel oil, roman chamomile oil, jasmine oil, extra virgin olive oil, saponified oil of coconut, saponified oil of palm, hemp seed oil, jojoba seed oil, or sunflower oil. In some embodiments, the cosmetic can include at least one of titanium dioxide white; one or more of the following iron oxides: black oxide, brown oxide, orange oxide, red oxide (red shade), red oxide (blue shade), yellow oxide; chromium oxide green; hydrated chromium oxide green; pluot purple; ultramarine blue; ultramarine violet; and ultramarine pink.

In some embodiments, the cosmetic need not be limited to any particular type of cosmetic. In some embodiments, the cosmetic can be, for example, a facial cosmetic, a lotion, a cream, e.g., an antiwrinkle cream, a sunscreen, a foundation, a lipstick, a gloss, a perfume, a deodorant, hair spray, shampoo, shaving cream, mascara, and/or an antiperspirant.

In some embodiments, the polymers and/or monomers of the acrylamide derivatives can be used in applications and compositions other than cosmetics. In some embodiments, the compounds can be used in cell growth media, as a scaffold material, in a hydrogel, as a food additive, in baby diapers, in organ manufacture, in tissue engineering, in tubing sieves, and/or in construction.

Method of Preparing

There are a variety of ways in which the various embodiments can be made. In some embodiments, the acrylamide derivatives can be made by the coupling reaction between an amine and an acid chloride. In some embodiments, the amine is on the carbohydrate unit (e.g., a pyranose unit) and is usually protected as the hydrochloride. In some embodiments, the acid chloride is a polymerizable functional unit such as acrylchoride. In some embodiments, there is no need to protect the hydroxyl units on the carbohydrate (e.g., pyran ring) as the amino moieties are much more reactive than hydroxyl moieties and as such couple with the amino exclusively.

Figure 5:
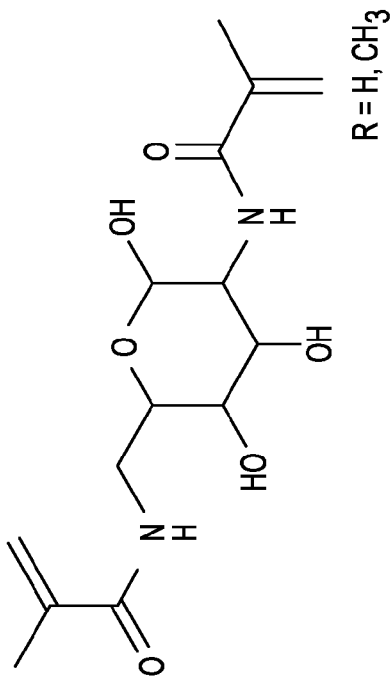
FIG. 5 is a depiction of a reaction diagram for some embodiments of the structure and synthesis of 2-methyl-N-[3,4,6-trihydroxy-5-(2-methyl-acryloylamino)-tetrahydro-pyran-2-ylmethyl]-acrylamide.
Figure 5:
Figure 5:
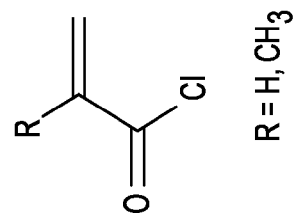
Figure 5:
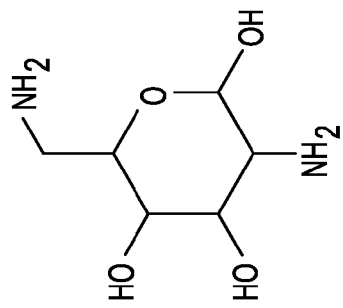

FIG. 3 depicts some embodiments for the synthesis of an acrylamide pyranose unit. Additional method of making various acrylamide pyranose units are outlined in Examples 1-4. For the bis amino structures, FIG. 5 depicts some embodiments of how some such molecules can be made and various further Examples are provided in Examples 5-7.

Method of Polymerizing

There are a variety of approaches to polymerizing one or more of the various monomers provided herein into a polymer.

In some embodiments, a method of preparing a polymer is provided. In some embodiments the method includes polymerizing one or more monomers to form a polymer. In some embodiments, the one or more monomers include a first monomer selected from the group of a monomer represented by Formula XIV, a monomer represented by Formula XV, and combinations thereof:

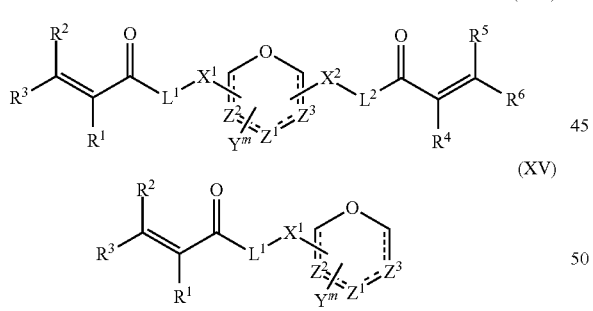

(XIV)

(XV)

wherein, $X^1$ is a bond or $-C_{1-6}$ alkylene-; $X^2$ is a bond or $-C_{1-6}$ alkylene-; $L^1$ is $-NH-$, S, or O; and $L^2$ is $-NH-$, S, or O; wherein, each $Y^m$ is independently hydrogen, hydroxy, saturated $C_1$-$C_{24}$ alkyl, unsaturated $C_2$-$C_{24}$ alkenyl, $C_2$-$C_{24}$ alkynyl, $-NR^AR^B$, $-NR^AC(O)R^B$, $-R^CNR^AR^B$, $-R^CNR^AC(O)R^B$, $-C(O)NR^AR^B$, $-OC(O)NR^AR^B$, $-C(O)R^A$, $-R^CC(O)R^A$, $-R^COC(O)R^A$, $-C(O)OR^A$, $-R^CC(O)OR^A$, $-OR^A$, $-R^COR^A$, $-SR^A$, $-R^CSR^A$, $-S(O)_q$, $-S(O)_qR^C$, $-OS(O)_q$, $-NS(O)_q$, $-NS(O)_qR^C$, $-P(O)_qR^C$, $-OP(O)_q$, $-NP(O)_q$, $-NP(O)_qR^C$, or a substituted version thereof, wherein each $R^A$ and $R^B$ is independently hydrogen, $C_1$-$C_6$ alkyl, unsaturated $C_2$-$C_6$ alkenyl, or $C_2$-$C_6$ alkynyl, each $R^C$ is a bond, or $-C_{1-6}$ alkylene-, wherein each q is independently one, two, or three, and m is an integer from 0 to 18; wherein $Z^1$, $Z^2$, and $Z^3$ are each independently a single bond, a double bond, $-CH_2-$, $-CH(OH)-$, $-CH=$, $-CH_2-CH_2-$, $=CH-CH_2-$, $=CH-CH=$, $-CH=CH-$, $-CH_2-CH_2-CH_2-$, $=CH-CH_2-CH_2-$, $=CH-CH_2-CH=$, $=CH-CH=CH-$, or $-CH=CH_2-CH_2-$ wherein each of $Z^1$, $Z^2$, and $Z^3$ is optionally substituted with one, two, three or four of $Y^m$, and wherein each of $Z^1$, $Z^2$, and $Z^3$ is optionally substituted with $X^1$ or $X^2$; wherein $R^1$, $R^2$, $R^3$, $R^4$, $R^5$, and $R^6$ are each independently hydrogen, $C_1$-$C_{24}$ alkyl, unsaturated $C_2$-$C_{24}$ alkenyl, $C_2$-$C_{24}$ alkynyl, or a substituted version thereof; and wherein each ═ is a double bond or a single bond.

In some embodiments, the one or more monomers do not include methacrylamide or acrylamide. In some embodiments, the amount of methacrylamide or acrylamide is so low as to be undetectable. In some embodiments, any amount of included methacrylamide or acrylamide is so low as to not contribute, structurally, to the formation of the polymer.

In some embodiments, the one or more monomers are represented by Formula XVI, XVII, XVIII or XIX:

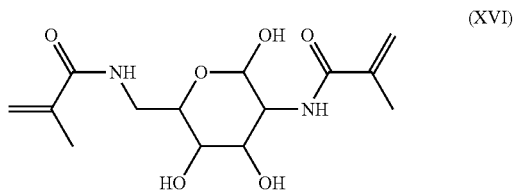

(XVI)

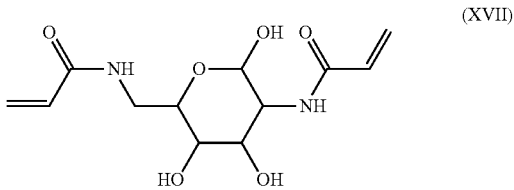

(XVII)

(XVIII)

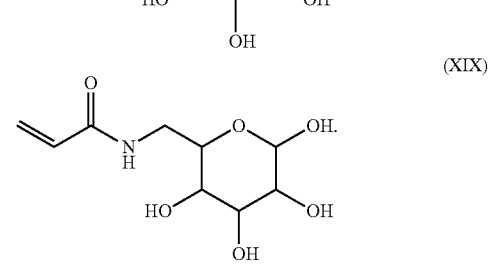

(XIX)

In some embodiments, there are a wide variety of polymerization techniques that are applicable and allow for tuning the acrylamide derivative. In some embodiments, polymerization is driven by a polymerization catalyst. In some embodiments, polymerization is achieved by UV exposure. In some embodiments, the acrylamide can be polymerized by free radicals. The radicals can be generated by thermal, photochemical, electrochemical, and/or redox means. However, some derivatives of the acrylamide can also be polymerized by anionic polymerization.

Nutrients to Skin

In some embodiments, the one or more of the monomers and/or polymers provided herein can be employed to provide nutrients to skin. In some embodiments, this can be achieved via the pathway depicted in FIG. 4 (e.g., allowing the breakdown of an acrylamide derivative into adenosine triphosphate and/or urea. In some embodiments, this can be achieved by the amount of water that can be present with the monomer and/or polymer of the acrylamide derivative.

In some embodiments, one or more of the sugar based acrylamide can be used to provide one or more nutrients to the skin. In some embodiments, the method includes providing a cosmetic composition that includes a polyacrylamide derivative, such as a pyranose polyacrylamide polymer or a pyranose polymethacrylamide polymer. In some embodiments, the composition can also include at least one cosmetic additive. In some embodiments, the composition includes less than about 0.2% by weight of acrylamide (including other ranges provided herein). In some embodiments, the method further includes applying the cosmetic composition to a subject's skin to provide nutrients to the subject's skin. In some embodiments, any, and any combination, of acrylamide derivatives (monomers and/or polymers) provided herein can be used to provide nutrients to the skin or to a subject.

In some embodiments, a method of providing nutrients to the skin is provided. In some embodiments, the method includes providing a cosmetic composition including a polymer (e.g., any of the polymers, or combinations thereof provided herein) and applying the cosmetic composition to a subject's skin to provide nutrients to the subject's skin. In some embodiments, the polymer includes one or more cross-linked monomer units, and wherein the cross-linked monomer units are represented by Formula XX:

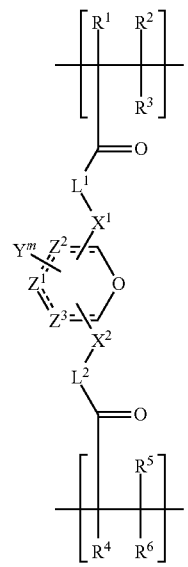

(XX)

wherein, $X^1$ is a bond or $-C_{1-6}$ alkylene-; $X^2$ is a bond or $-C_{1-6}$ alkylene-; and $L^1$ is $-NH-$, S, or O; $L^2$ is $-NH-$, S, or O; wherein each $Y^m$ is independently hydrogen, hydroxy, saturated $C_1$-$C_{24}$ alkyl, unsaturated $C_2$-$C_{24}$ alkenyl, $C_2$-$C_{24}$ alkynyl, $-NR^AR^B$, $-NR^AC(O)R^B$, $-R^CNR^AR^B$, $-R^CNR^AC(O)R^B$, $-C(O)NR^AR^B$, $-OC(O)NR^AR^B$, $-C(O)R^A$, $-R^CC(O)R^A$, $-R^COC(O)R^A$, $-C(O)OR^A$, $-R^CC(O)OR^A$, $-OR^A$, $-R^COR^A$, $-SR^A$, $-R^CSR^A$, $-S(O)_q$, $-S(O)_qR^C$, $-OS(O)_q$, $-NS(O)_q$, $-NS(O)_qR^C$, $-P(O)_qR^C$, $-OP(O)_q$, $-NP(O)_q$, $-NP(O)_qR^C$, or a substituted version thereof, wherein each $R^A$ and $R^B$ is independently hydrogen, $C_1$-$C_6$ alkyl, unsaturated $C_2$-$C_6$ alkenyl, or $C_2$-$C_6$ alkynyl, each $R^C$ is a bond, or $-C_{1-6}$ alkylene-, wherein each q is independently one, two, or three, and n is an integer from 0 to 18. In some embodiments, $Z^1$, $Z^2$, and $Z^3$ are each independently a single bond, a double bond, $-CH_2-$, $-CH(OH)-$, $-CH=$, $-CH_2-CH_2-$, $=CH-CH_2-$, $=CH-CH=$, $-CH=CH-$, $-CH_2-CH_2-CH_2-$, $=CH-CH_2-CH_2-$, $=CH-CH_2-CH=$, $=CH-CH=CH-$, or $-CH=CH_2-CH_2-$ wherein each of $Z^1$, $Z^2$, and $Z^3$ is optionally substituted with one, two, three or four of $Y^m$, and wherein each of $Z^1$, $Z^2$, and $Z^3$ is optionally substituted with $X^1$ or $X^2$; wherein, $R^1$, $R^2$, $R^3$, $R^4$, $R^5$, and $R^6$ are each independently hydrogen, $C_1$-$C_{24}$ alkyl, unsaturated $C_2$-$C_{24}$ alkenyl, $C_2$-$C_{24}$ alkynyl, or a substituted version thereof; and wherein each ═ is a double bond or a single bond.

In some embodiments, the polymer added can be that represented by Formula XXI or XXII:

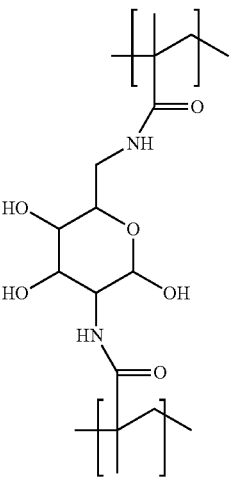

(XXI)

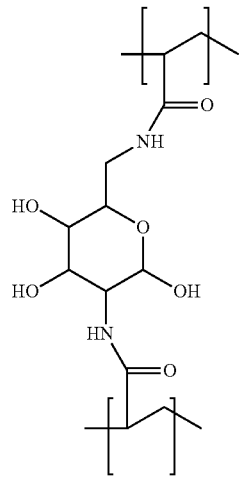

(XXII)

In some embodiments, the polymer includes one or more monomer units represented by Formula XXIII:

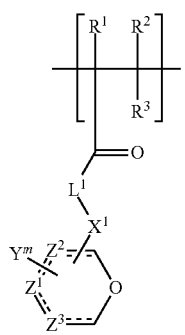

(XXIII)

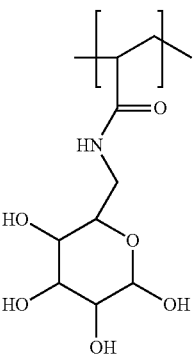

XXV wherein, $X^1$ is a bond or —$C_{1-6}$ alkylene-; and $L^1$ is —NH—, S, or O; wherein each $Y^m$ is independently hydrogen, hydroxy, saturated $C_1$-$C_{24}$ alkyl, unsaturated $C_2$-$C_{24}$ alkenyl, $C_2$-$C_{24}$ alkynyl, —$NR^AR^B$, —$NR^AC(O)R^B$, —$R^C$-$NR^AR^B$, —$R^CNR^AC(O)R^B$, —$C(O)NR^AR^B$, —$OC(O)NR^AR^B$, —$C(O)R^A$, —$R^CC(O)R^A$, —$R^COC(O)R^A$, —$C(O)OR^A$, —$R^CC(O)OR^A$, —$OR^A$, —$R^COR^A$, —$SR^A$, —$R^CSR^A$, —$S(O)_q$, —$S(O)_qR^C$, —$OS(O)_q$, —$NS(O)_q$, —$NS(O)_qR^C$, —$P(O)_qR^C$, —$OP(O)_q$, —$NP(O)_q$, —$NP(O)_qR^C$, or a substituted version thereof, wherein each $R^A$ and $R^B$ is independently hydrogen, $C_1$-$C_6$ alkyl, unsaturated $C_2$-$C_6$ alkenyl, or $C_2$-$C_6$ alkynyl, each $R^C$ is a bond, or —$C_{1-6}$ alkylene-, wherein each q is independently one, two, or three, and n is an integer from 0 to 19; wherein, $Z^1$, $Z^2$, and $Z^3$ are each independently a single bond, a double bond, —$CH_2$—, —$CH(OH)$—, —$CH$=, —$CH_2$—$CH_2$—, =$CH$—$CH_2$—, =$CH$—$CH$=, —$CH$=$CH$—, —$CH_2$—$CH_2$—$CH_2$—, =$CH$—$CH_2$—$CH_2$—, =$CH$—$CH_2$—$CH$=, =$CH$—$CH$=$CH$—, or —$CH$=$CH_2$—$CH_2$— wherein each of $Z^1$, $Z^2$, and $Z^3$ is optionally substituted with one, two, three or four of $Y^m$, and wherein each of $Z^1$, $Z^2$, and $Z^3$ is optionally substituted with $X^1$ or $X^2$; wherein $R^1$, $R^2$, and $R^3$, are each independently hydrogen, $C_1$-$C_{24}$ alkyl, unsaturated $C_2$-$C_{24}$ alkenyl, $C_2$-$C_{24}$ alkynyl, or a substituted version thereof and wherein each ══ is a double bond or a single bond.

In some embodiments, the polymer that can be used is represented by Formula XXIV or XXV:

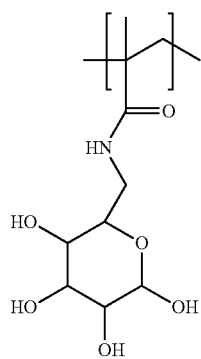

XXIV

The type of skin that the nutrients are applied to can be any of a variety of types, including skin that is also in contact with cosmetics. In some embodiments, the skin is the skin of a subject's face. In some embodiments, the skin can be around the nose, mouth, eyes, and/or ears. In some embodiments, the skin can include leg, arm, back, etc. In some embodiments, the skin is human. In some embodiments, the skin is another animal's skin, such as pets, food source animals, and/or farm animals. In some embodiments, one or more of the derivatives provided herein have a lower risk and/or likelihood of inducing allergies to a subject who is allergic to traditional forms of polyacrylamide.

EXAMPLES

Example 1

SYNTHESIS OF N-(3,4,5,6-TETRAHYDROXY-TETRAHYDRO-PYRAN-2-YLMETHYL)-ACRYLAMIDE

N-(6-deoxy-D-galactose)-acrylamide is synthesized by means of acid chloride coupling mediated by an organic base. Anhydrous THF (500 mL) is added to a flame dried 1 L three neck flask and flooded with argon. To the THF is added 30.0 g (139.5 mmol) of anhydrous 6-amino-6-deoxy-D-galactose hydrochloride and 15.6 g (197.2 mmol) anhydrous pyridine and allowed to dissolve at a temperature of −20 degrees Centigrade. Then, by drop wise addition, 13.1 g (140.5 mmol) of acrylchloride in 50 mL of dry THF is added to the 6-amino-6-deoxy-D-galactose solution at room temperature followed by warming to 25 degrees Centigrade. The reaction is allowed to proceed for five hours at 25 degrees Centigrade. The pyridinium chloride is then removed by filtration followed by washing and the solvents removed by rotary evaporation and high vacuum to yield N-(6-deoxy-D-galactose)-acrylamide. The general reaction scheme is shown in FIG. 3.

Example 2

SYNTHESIS OF N-(6-DEOXY-D-GALACTOSE)-METHACRYLAMIDE

Using a similar procedure as outlined in Example 1, 6-amino-6-deoxy-D-glucose is reacted with methacrylic chloride to yield N-(6-deoxy-D-galactose)-methacrylamide.

Example 3

SYNTHESIS OF N-(6-DEOXY-D-GALACTOSE)-ACRYLAMIDE

Using a similar procedure as outlined in Example 1 pyridine is replaced with 200 mmol of potassium carbonate to yield N-(6-deoxy-D-galactose)-acrylamide.

Example 4

SYNTHESIS OF N-(3,4,5,6-TETRAHYDROXY-TETRAHYDRO-PYRAN-2-YLMETHYL)-ACRYLAMIDE

The present example outlines a method of synthesis of N-(3,4,5,6-tetrahydroxy-tetrahydro-pyran-2-ylmethyl)-acrylamide by means of a biphase system. N-(6-deoxy-D-galactose)-acrylamide is synthesized by means of acid chloride coupling. Anhydrous THF (500 mL) is added to a flame dried 1 L three neck flask and flooded with argon. To 150 mL of water is added 30.0 g (139.5 mmol) of anhydrous 6-amino-6-deoxy-D-galactose hydrochloride and the solution is neutralized with 3.4 g (139.6 mmol) sodium hydroxide and allowed to dissolve. A solution of 13.1 g (140.5 mmol) of acrylchloride in 100 mL of methylene chloride is added to the 6-amino-6-deoxy-D-galactose water solution at room temperature and stirred rapidly to form an emulsion. The reaction is allowed to proceed for five hours at 25 degrees Centigrade. The stirring is stopped and the phases are allowed to separate. The methylene chloride layer is extracted and the water layer is washed with three 25 mL portions of methylene chloride. The methylene chloride samples are combined, dried, and then the solvent is removed by rotary evaporation and high vacuum to yield N-(6-deoxy-D-galactose)-acrylamide.

Example 5

SYNTHESIS OF 2-METHYL-N-[3,4,6-TRIHYDROXY-5-(2-METHYL-ACRYLOYLAMINO)-TETRAHYDRO-PYRAN-2-YLMETHYL]-ACRYLAMIDE

An outline of the synthesis is provided in FIG. 5. A multi-functional cross-linking agent is created from 2,6-diamino-2,6-dideoxy-D-glucose, methacrylic chloride and is mediated by an organic base. Anhydrous THF (500 mL) is added to a flame dried 1 L three neck flask and flooded with argon. To the THF is added 38.6 g (153.7 mmol) of 2,6-diamino-2,6-dideoxy-D-glucose hydrochloride and 32.5 g (411.3 mmol) pyridine and allowed to dissolve. Then, by drop wise addition, 33.2 g (317.4 mmol) of methacrylic chloride in 55 mL of dry THF is added to the 2,6-diamino-2,6-dideoxy-D-galactose solution at −20 degrees Centigrade followed by warming to room temperature. The reaction is allowed to proceed for five hours at room temperature. The pyridinium chloride is then removed by filtration followed by washing and the solvents removed by rotary evaporation and high vacuum to yield N,N-(2,6-deoxy-D-glucose)-2,6-acrylamide.

Example 6

SYNTHESIS OF N,N-(2,6-DEOXY-D-GALACTOSE)-2,6-ACRYLAMIDE

Using a similar procedure as outlined in Example 4, 2,6-diamino-2,6-dideoxy-D-galactose is reacted with acrylchloride to yield N,N-(2,6-deoxy-D-galactose)-2,6-acrylamide.

Example 7

SYNTHESIS OF N,N-(2,6-DEOXY-D-GLUCOSE)-2,6-ACRYLAMIDE

Using a similar procedure as outlined in Example 4, pyridine is replaced with 412 mmol of potassium carbonate to yield N,N-(2,6-deoxy-D-glucose)-2,6-acrylamide.

In some embodiments, the acrylamide pyranose derivatives can be used as a hydrogel and/or polymer fixative in cosmetic products. In some embodiments, these compositions have increased safety. The following examples are directed to some such embodiments.

Example 8

Preparation of Linear Acrylamide Pyranose Polymer (pAAP)

In a four-neck 500 ml separable flask equipped with a mechanical stirrer, a dropping funnel, and a condenser, N-(6-deoxy-D-galactose)-acrylamide monomer (NMA), 20 g; distilled water, 50 ml; and tetrahydrofuran, 150 ml, are combined. The flask is warmed up to 60 degrees Centigrade under air with stirring, and a specified amount of 2,2'-azobis(4-methoxy-2,4-dimethylvaleronitrile) is added as a polymerization initiator. The solution will change into a gel-like material in about 20 min. This point is tentatively taken as a standard for the end of reaction.

Disappearance of monomer at this point can be confirmed by silica gel thin layer chromatography (TLC). After the reaction, the reaction mixture is concentrated under reduced pressure at room temperature, and remaining water in the viscous liquid is removed by freeze-drying to isolate poly (N-(6-deoxy-D-galactose)-acrylamide), pAAP, as a white solid.

Example 9 pAAP Hydrogels 2.7 g of N-(6-deoxy-D-glucose)-acrylamide and 0.3 g of 2-methyl-N-[3,4,6-trihydroxy-5-(2-methyl-acryloylamino)-tetrahydro-pyran-2-ylmethyl]-acrylamide are added to 6 mL of distilled water and mixed thoroughly. Propylene glycol (3 ml) is added to the solution followed by the addition 0.2 g of Darocur 1173. The solution is then exposed to UV light at 350 nm for 5 min which initiates the polymerization thereby forming a hydrogel.

Example 10 pAAP Methacrylate Copolymer

To a 3-neck reaction kettle outfitted with a condenser, argon inlet, and stirrer 10.0 g of N-(6-deoxy-D-galactose)-acrylamide, 4.0 g acrylic acid, 6.0 g of ethyl methacrylate, and 60 mL of THF are combined and mixed thoroughly. The solution is deoxygenated and warmed to 70 degrees Centigrade. To the warmed solution, 5 mL of a 5% AIBN in THF solution is added by dropwise addition. The reaction is allowed to proceed for 36 hours. The liquor is precipitated by a 50-50 mixture of ethanol/hexanes three times. The polymer is collected by filtration and dried under vacuum to yield a white solid of a pAAP methacrylate copolymer.

Example 11 pAAP/Sodium Acryloyldimethyltaurate Copolymer

To a 3-neck reaction kettle outfitted with a condenser, argon inlet, and stirrer is added 10.0 g of N-(6-deoxy-D-galactose)-acrylamide, 6.0 g sodium acryloyldimethyltaurate and 60 mL of water and mixed thoroughly. The solution is deoxygenated and warmed to 70 degrees Centigrade. To the warmed solution, 5 mL of a 6% (w/v) ammonium persulfate and 12% (w/v) sodium metabisulfite solution are added. The reaction is allowed to proceed for 36 hours. After the reaction, the reaction mixture is concentrated under reduced pressure at room temperature, and remaining water in the viscous liquid is removed by freeze-drying to isolate the copolymer as a white solid of pAAP/sodium acryloyldimethyltaurate copolymer.

While not limiting to the present scope, the following examples put forth exemplary sample formulations.

Example 12

Sample Hair Spray Formulation

A combination of Ethanol 34.0 wt. %, pAAP copolymer (Example 10) 8.0 wt. %, 2-amino-2-methyl-1-propanol 0.6 wt. %, fragrance 0.2 wt. %, n-pentane 8.0 wt. %, dimethyl ether 28.0 wt. %, water to 100.0% is prepared. Fragrance is a mixture of vanilla 34.8%, sandalwood 26.1%, French lavender 17.4%, jasmine 8.7%, ylang ylang 8.7% and dark musk was 4.2%.

Example 13

Sample Hair Spray Formulation

A combination of ethanol 34.5 wt. %, pAAP linear polymer (Example 8) 8.2 wt. %, fragrance 0.2 wt. %, n-pentane 8.3 wt. %, dimethyl ether 27.6 wt. %, is mixed with water to 100.0%. Fragrance is a mixture of vanilla 34.8%, sandalwood 26.1%, French lavender 17.4%, jasmine 8.7%, ylang ylang 8.7% and dark musk was 4.2%. This provides a hair spray formulation.

Example 14

Sample Shampoo Formulation

To 26.0 g of 30% by weight solution of ammonium lauryl sulfate in water (99 g) is added 0.3 g fragrance mixture (vanilla 34.8%, sandalwood 26.1%, French lavender 17.4%, jasmine 8.7%, ylang ylang 8.7% and dark musk was 4.2%) to create a starting surfactant mixture (SSM). To 20.0 g of the SSM is added 3.0 g of 30% water solution of pAAP (Example 8) followed by 2.0 g of cocamide diethanolamine and then 5.0 g cocamidopropyl betaine. The pH is then adjusted to 5.7-6.1 using citric acid. This provides a shampoo formulation formulation.

Example 15

Sample Shaving Cream Formulation

A solution of 4.0 g glycerin, 1.0 g coco glucoside/glyceryl oleate, 4.0 g cetyl betaine, 5.0 g sodium cocosulfate, and 0.1 g tetrasodium EDTA is made and warmed to 70 degrees Centigrade. To this is added 0.1 g acrylamide pyranose copolymer from Example 11 with vigorous stirring. With continued mixing, 48.0 g of disodium lauryl sulfosuccinate is slowly added and mixed until homogenous. Then 0.5 g of a mixture of propylene glycol; diazolidinyl urea; iodopropynyl butyl carbomate is added followed by 0.5 g of sodium chloride and 0.3 g fragrance (vanilla 34.8%, sandalwood 26.1%, French lavender 17.4%, jasmine 8.7%, ylang ylang 8.7% and dark musk was 4.2%.). Mixing is continued until homogenous. This provides shaving cream formulation.

Example 16

Mascara Formulation

Mixture 1 is created by combining 6.0 g of mica black, 3.0 g of Ronastar Golden Sparks, 1.0 g of Ronastar Nobel sparks, and 2.0 g of satin mica. Mixture 2 is created by heating to 85 degrees Centigrade and mixing 3.0 g beeswax white, 3.5 g Syncrowax HRC, 5.0 g stearic acid, 3.5 g Tegin M, 2.5 g Tegosoft CT, 2.0 g Dow Corning 556, 0.5 g tocopherol acetate, and 0.8 g of phenonip. To mixture 2 is added 3.5 g of pAAP copolymer powder from Example 11. Mixture 3 is created from 59.2 g of water, 1.25 g 2-amino-2-methyl-1-propanol, 1.0 g 1,3-butanediol, and 0.5 g Rona-Care Biotin Plus. Mixture 4 is created from 0.3 g of Germall 115 and 1.5 g of water.

Mixture 3 is heated to 85 degrees Centigrade and mixture 1 added to mixture 3 with vigorous stirring. The combined mixture of 1 and 3 are added to mixture 2 at 85 degrees Centigrade with stirring. The mixture is cooled to 40 degrees Centigrade and mixture 4 is then added. Continue stirring until homogenous and cool to room temperature. This produces a mascara formulation.

Example 17

Polymerized Acrylamide and Methacrylamide

The acrylamide of the 6-amino-D-glucose and the methacrylamide of the 6-amino-D-glucose are separately collected and are separately polymerized in water as a 20% solution using 4,4'-azobis(4-cyanovaleric acid) at 75 degree Centigrade under argon. This produces the resulting polymer of the acrylamide of the 6-amino-D-glucose and the polymer of the methacrylamide of the 6-amino-D-glucose.

Unless otherwise specified, the section headings are not to be taken as excluding the combinations and/or variations of embodiments in other sections and are being used for convenience only. In regard to the text and figures of the detailed description, in some embodiments, the structures depicted as his amino derivatives can be applied in a mono amino setting, simply by the removal of one of the nitrogen groups. Similarly, the structures depicted as mono amino derivatives can be applied in a his amino setting, simply by the addition of one nitrogen group as appropriate. Similarly, compositions and/or monomer embodiments can be formed into their polymeric versions (in either a homogeneous or heterogeneous manner) and that the polymers depicted also describe the monomeric forms. These aspects, of course, do not apply to the claims.

The present disclosure is not to be limited in terms of the particular embodiments described in this application, which are intended as illustrations of various aspects. Many modifications and variations can be made without departing from its spirit and scope, as will be apparent to those skilled in the art. Functionally equivalent methods and apparatuses within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, reagents, compounds, compositions or biological systems, which can, of course, vary. It is also to be understood that the terminology used herein is for the purpose of describing particular embodiments only, and is not intended to be limiting.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (e.g., the bare recitation of "two recitations," without other modifiers, means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, such as in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," and the like include the number recited and refer to ranges which can be subsequently broken down into subranges as discussed above. Finally, as will be understood by one skilled in the art, a range includes each individual member. Thus, for example, a group having 1-3 cells refers to groups having 1, 2, or 3 cells. Similarly, a group having 1-5 cells refers to groups having 1, 2, 3, 4, or 5 cells, and so forth.

From the foregoing, it will be appreciated that various embodiments of the present disclosure have been described herein for purposes of illustration, and that various modifications may be made without departing from the scope and spirit of the present disclosure. Accordingly, the various embodiments disclosed herein are not intended to be limiting, with the true scope and spirit being indicated by the following claims.

The invention claimed is:

1. A cosmetic composition comprising a polymer and at least one cosmetic additive, wherein the polymer comprises one or more cross-linked monomer units, wherein the cross-linked monomer units are represented by Formula IV or V:

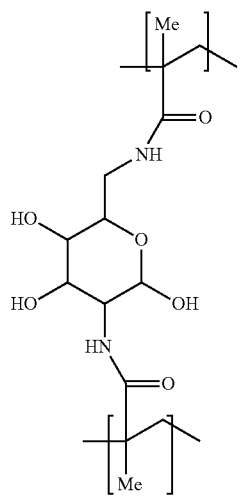
(IV)

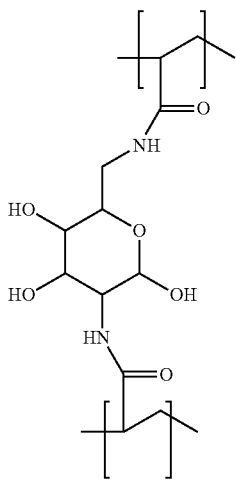
(V)

2. The cosmetic composition of claim 1, wherein the polymer comprises less than about 1% by weight of acrylamide monomer units.

3. A method comprising:
applying a cosmetic composition comprising a polymer and at least one cosmetic additive to a subject's skin, wherein the polymer comprises one or more cross-linked monomer units, and wherein the cross-linked monomer units are represented by Formula IV or V:

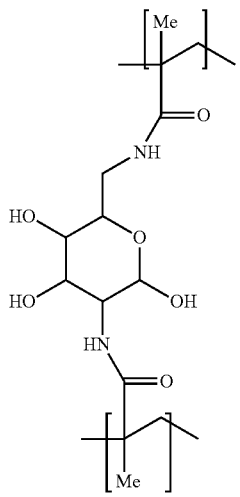
(IV)

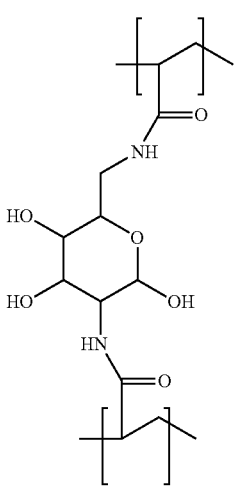
(V)

4. The cosmetic composition of claim 1, wherein the cosmetic additive comprises one or more of denatured alcohol, alkyl benzoate $C_{12}$-$C_{15}$, allantoin, alpha-isomethyl ionone, aluminum chlorohydrate, water, wax, ascorbyl palmitate, butane, butyrospermum parkii, hydroxyethyl-cellulose, hydroxypropyl-cellulose, isobutane, isopentane, propane, castor oil, dye, triethanolamine, purified water, sodium lauryl sulfate, sodium laureth sulfate, olefin sulfonate, cocamidopropyl betaine, decyl glucoside, citric acid, paraben, emulsifying wax, beeswax, vegetable glycerin, oat bran, passion fruit juice, red rose water, raspberry extract, yucca herbal extract, aloe vera leaf gel, tea tree oil, peppermint leaf oil, spearmint leaf oil, wintergreen leaf oil, lavender oil, cinnamon leaf oil, lemon Peel oil, valencia orange peel oil, pink grapefruit peel oil, roman chamomile oil, jasmine oil, extra virgin olive oil, saponified oil of coconut, saponified oil of palm, hemp seed oil, jojoba seed oil, and sunflower oil.

5. The cosmetic composition of claim 1, wherein the cosmetic composition further comprises at least one of titanium dioxide white, black iron oxide, brown iron oxide, orange iron oxide, red iron oxide (red shade), red iron oxide (blue shade), yellow iron oxide, chromium oxide green, hydrated chromium oxide green, pluot purple, ultramarine blue, ultramarine violet, and ultramarine pink.

6. The cosmetic composition of claim 1, wherein the cosmetic composition comprises less than about 0.2% by weight of acrylamide monomer units.

7. The cosmetic composition of claim 1, wherein the cosmetic composition comprises no detectable amount of acrylamide monomer and methacrylamide monomer.

8. The method of claim 3, wherein the cosmetic additive comprises one or more of denatured alcohol, alkyl benzoate $C_{12}$-$C_{15}$, allantoin, alpha-isomethyl ionone, aluminum chlorohydrate, water, wax, ascorbyl palmitate, butane, butyrospermum parkii, hydroxyethyl-cellulose, hydroxypropyl-cellulose, isobutane, isopentane, propane, castor oil, dye, triethanolamine, purified water, sodium lauryl sulfate, sodium laureth sulfate, olefin sulfonate, cocamidopropyl betaine, decyl glucoside, citric acid, paraben, emulsifying wax, beeswax, vegetable glycerin, oat bran, passion fruit juice, red rose water, raspberry extract, yucca herbal extract, aloe vera leaf gel, tea tree oil, peppermint leaf oil, spearmint leaf oil, wintergreen leaf oil, lavender oil, cinnamon leaf oil, lemon Peel oil, valencia orange peel oil, pink grapefruit peel oil, roman chamomile oil, jasmine oil, extra virgin olive oil, saponified oil of coconut, saponified oil of palm, hemp seed oil, jojoba seed oil, and sunflower oil.

9. The method of claim 3, wherein the cosmetic composition further comprises at least one of titanium dioxide white, black iron oxide, brown iron oxide, orange iron oxide, red iron oxide (red shade), red iron oxide (blue shade), yellow iron oxide, chromium oxide green, hydrated chromium oxide green, pluot purple, ultramarine blue, ultramarine violet, and ultramarine pink.

10. The method of claim 3, wherein the polymer comprises less than about 1% by weight of acrylamide monomer units.

11. The method of claim 3, wherein the cosmetic composition comprises less than about 0.2% by weight of acrylamide monomer units.

12. The method of claim 3, wherein the cosmetic composition comprises no detectable amount of acrylamide monomer and methacrylamide monomer.

* * * * *